(12) United States Patent
Taussig et al.

(10) Patent No.: US 6,620,587 B1
(45) Date of Patent: Sep. 16, 2003

(54) RIBOSOME COMPLEXES AS SELECTION PARTICLES FOR IN VITRO DISPLAY AND EVOLUTION OF PROTEINS

(75) Inventors: Michael John Taussig, Cambridge (GB); Mingyue He, Cambridge (GB)

(73) Assignee: Discerna Limited, Cambridge (GB)

( * ) Notice: Subject to any disclaimer, the term of this patent is extended or adjusted under 35 U.S.C. 154(b) by 0 days.

(21) Appl. No.: 09/424,712

(22) PCT Filed: May 28, 1998

(86) PCT No.: PCT/GB98/01564

§ 371 (c)(1),
(2), (4) Date: Jan. 28, 2000

(87) PCT Pub. No.: WO98/54312

PCT Pub. Date: Dec. 3, 1998

(30) Foreign Application Priority Data

| May 28, 1997 | (GB) | 9710829 |
| Nov. 26, 1997 | (GB) | 9724850 |
| Feb. 28, 1998 | (GB) | 9804195 |

(51) Int. Cl.[7] ............... G01N 33/53; G01N 33/566; C12Q 1/00
(52) U.S. Cl. ............... 435/7.1; 435/4; 435/6; 435/69.1; 435/69.6; 435/DIG. 3; 435/DIG. 15; 435/DIG. 17; 436/501; 436/547
(58) Field of Search ............... 435/6, 7.1, 4, 69.1, 435/69.6, DIG. 3, DIG. 15, DIG. 17; 436/501, 547

(56) References Cited

FOREIGN PATENT DOCUMENTS

| WO | JP6178688 | 6/1994 |
| WO | WO95/11922 | 5/1995 |
| WO | WO01/75097 A2 | 10/2001 |

OTHER PUBLICATIONS

He et al., Nucleic Acids Research 25(24): 5132–5134 (1997).

He et al., Immunology 84: 662–668 (1995).

Hanes., Proc. Natl. Acad. Sci USA 94: 4937–4942 (1997).

Mattheakis et al., Methods in Enzymology 267: 195–207 (1996).

*Primary Examiner*—Andrew Wang
*Assistant Examiner*—Thomas Friend
(74) *Attorney, Agent, or Firm*—Heller Ehrman White & McAuliffe

(57) ABSTRACT

The invention provides a method of displaying nascent proteins or peptides as complexes with eukaryotic ribosomes and the mRNA encoding the protein or peptide following transcription and translation in vitro, of further selecting complexes carrying a particular nascent protein or peptide by means of binding to a ligand, antigen or antibody, and of subsequently recovering the genetic information encoding the protein or peptide from the selected ribosome complex by reverse transcription and polymerase chain reaction (RT-PCR). The RT-PCR recovery step is carried out directly on the intact ribosome complex, without prior dissociation to release the mRNA, thus contributing to maximal efficiency and sensitivity. The steps of display, selection and recovery can be repeated in consecutive cycles. The method is exemplified using single-chain antibody constructs as antibody-ribosome-mRNA complexes (ARMs).

34 Claims, 22 Drawing Sheets

Figure 1:
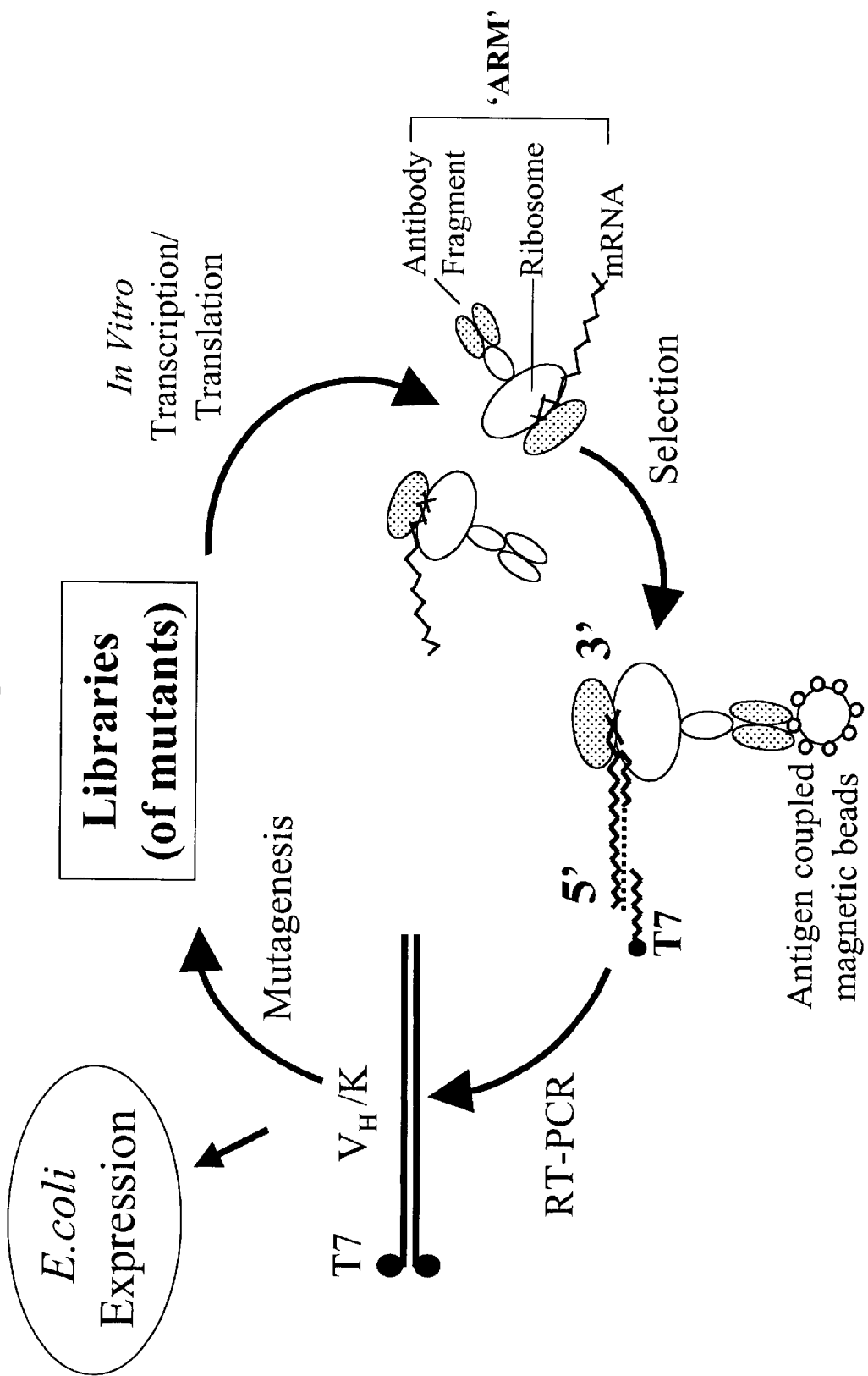

FIG. 2A
[SEQ ID1]

*T7 primer*
5'-gcgcgaatacgactcactatagagggacaaaccatgsaggtsmarctcgagsagtcwgg
                                                          VH ->
acctgagctgaagaagcctggagagacagtcaagatctcctgcaaggcttctgggtatgcct
tcaaaaactatggagtgaactgggtgaaggaggctccaggaaaggatttaaagtggatgggc
                    H35
tggataaacatctacactggggagccaacatatgttgatgacttcaagggacggtttgcctt
ctctttggaaacctctgccagcactgcctatttggagatcaacaacctcaaaaatgaagaca
cggcaacgtatttctgtacaagaggtgactacgtcaactggtacttcgatgtctggggcgca
                                          H100
gggaccacggtcaccgtctcctcagccaaaacgacacccccatctgtctatccactggccga
        linker ->
gctcgtgatgacccagattccactctccctgcctgtcaatcttggagatcaagcctccatct
      V$_L$ ->
cttgcagatctagtcagagccttgtacacagtaatggaaacacctatttacattggtacctg
cagaagccaggccagtctccaaagctcctgatctacaaagtttccaaccgattttatggggt
cccagacaggttcagtggcagtggatcagggacagatttcacactcaagatcagcagagtgg
aggctgaggatctgggaatttatttctgctctcaaagttcacatgttcctccgacgttcggt
ggaggcaccaagctggaaatcaaacgggctgatgctgcaccaactgtatccatcttcccacc
              Ck ->                                   *ggtagaagggtgg*
                                                              *D4 primer*
atccagtgagcagttaacatctggaggtgcctcagtcgtgtgcttcttgaacaacttctacc
*taggtc-5'*                                                  *gaacttgttgaagatgg*
                                                               *D3 primer*
ccaaagacatcaatgtcaagtggaaaattgatggcagtgaacgacaaaatggcgtcctgaac
*gg-5'*
agttggactgatcaggacagcaaagacagcacctacagcatgagcagcaccctcacgttgac
                                                            *gtactcgtcgtgggagtgc-5'*
                                                            *D2 primer*
caaggacgagtatgaacgacataacagctatacctgtgaggccactcacaagacatcaactt
cacccattgtcaagagcttcaacaggaatgagtgaggtggatccagtgca-3'
           *tcgaagttgtccttactcactccacctaggtcacgt-5'*
           *D1 primer*

FIG. 2B
[SEQ ID2]

T7 primer
5'-gcgcgaatacgactcactatagagggacaaaccatgsaggtsmarctcgagsagtcwgg
　　　　　　　　　　　　　　　　　　　V$_H$ ->
Acctgagctgaagaagcctggagagacagtcaagatctcctgcaaggcttctgggtatgcct
Tcaaaaactatggagtgaactgggtgaaggaggctccaggaaaggatttaaagtggatgggc
　　　　　　　H35
tggataaacatctacactggggagccaacatatgttgatgacttcaagggacggtttgcctt
ctctttggaaacctctgccagcactgcctatttggagatcaacaacctcaaaaatgaagaca
cggcaacgtatttctgtacaagaggtgactacgtcaactggtacttcgatgtctggggcgca
　　　　　　　　　　　　　　H100
gggaccacggtcaccgtctcctcagccaaaacgacacccccatctgtctatccactggccga
　　　　linker ->
gctcgtgatgacccagattccactctccctgcctgtcaatcttggagatcaagcctccatct
　　　　　V$_L$ ->
cttgcagatctagtcagagccttgtacacagtaatggaaacacctatttacattggtacctg
cagaagccaggccagtctccaaagctcctgatctacaaagtttccaaccgatttatggggt
cccagacaggttcagtggcagtggatcagggacagatttcacactcaagatcagcagagtgg
aggctgaggatctgggaatttatttctgctctcaaagttcacatgttcctccgacgttcggt
ggaggcaccaagctggaaatcaaacgggctgatgctgcaccaactgtatccatcttcccacc
　　　　　　　　Ck ->
atccagtgagcagttaacatctggaggtgcctcagtcgtgtgcttcttgaacaacttctacc
ccaaagacatcaatgtcaagtggaaaattgatggcagtgaacgacaaaatggcgtcctgaac
agttggactgatcaggacagcaaagacagcacctacagcatgagcagcaccctcacgttgac
　　　　　　　　　　　　　　　D2 primer: gtactcgtcgtgggagtgc-5'
　　　　　　　　　　　　　　　EVOU primer:　gtactcgtcgtgggagtgcaactg
caaggacgagtatgaacgacataacagctatacctgtgaggccactcacaagacatcaactt
gttcctgctcatacttgctgtattgtcgatatggacactccggagatctcg-5'
　　　　　　　　　　　　　　　　　　　　　　　　　XbaI
cacccattgtcaagagcttcaacaggaatgagtgaggtggatccagtgca-3'
　　　　tcgaagttgtccttactcactccacctaggtcacgt-5'
　　　　D1 primer 3' end of ARM mRNA is inaccessible in RT-PCR ARM Cycles: Full length DNA recovery by three primer RT-PCR

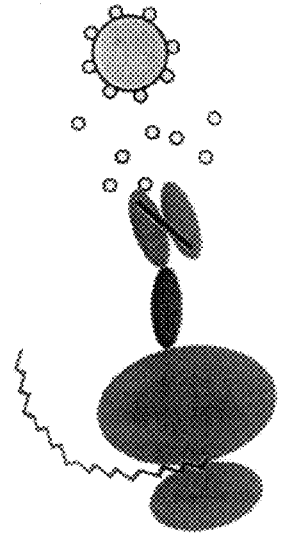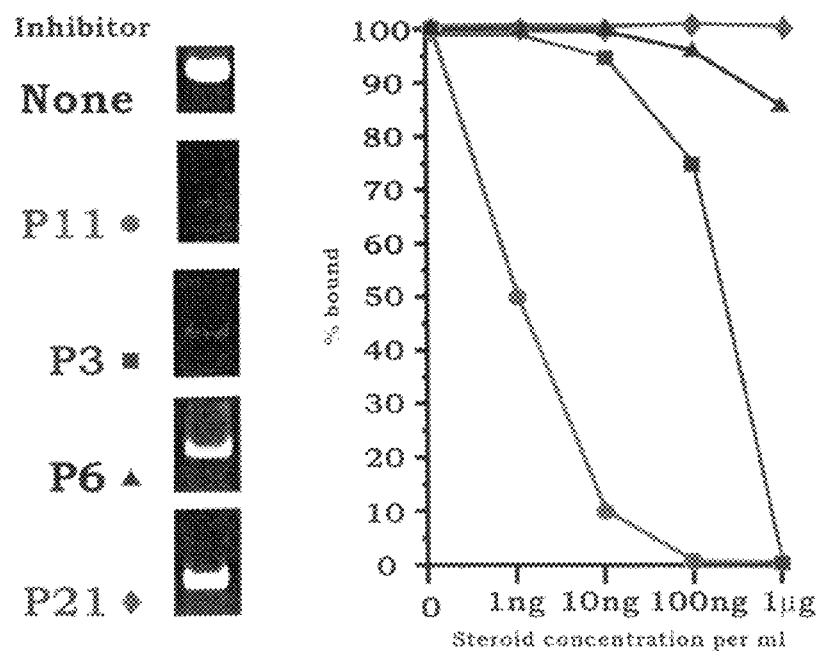
FIG. 6

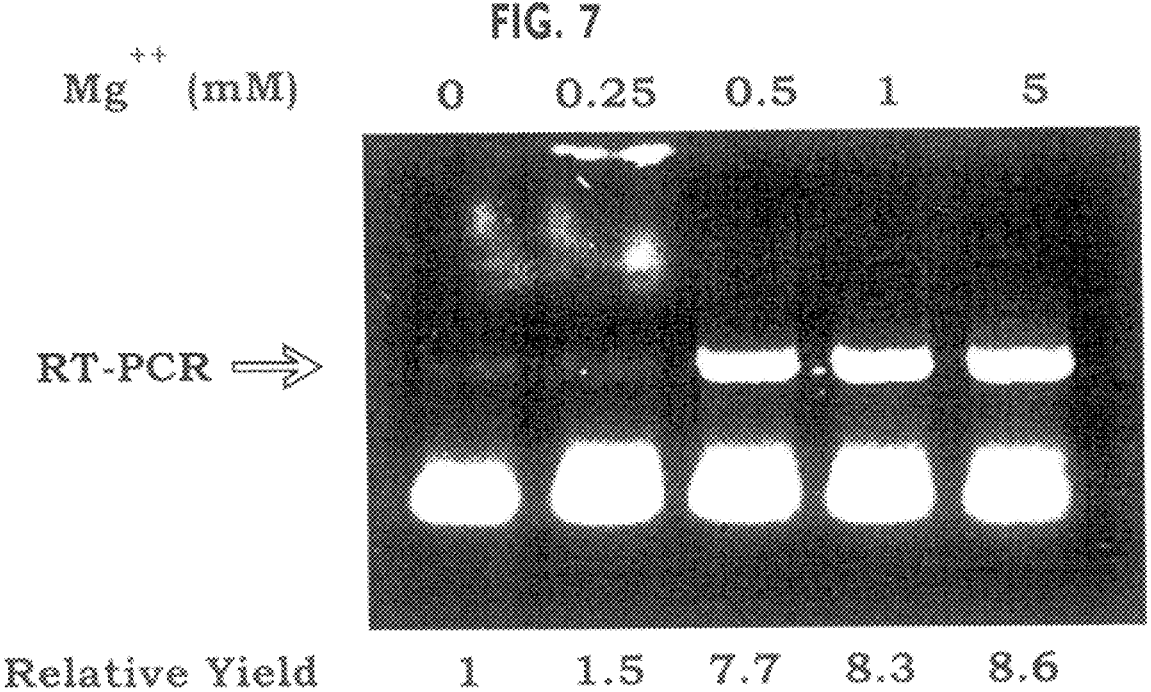

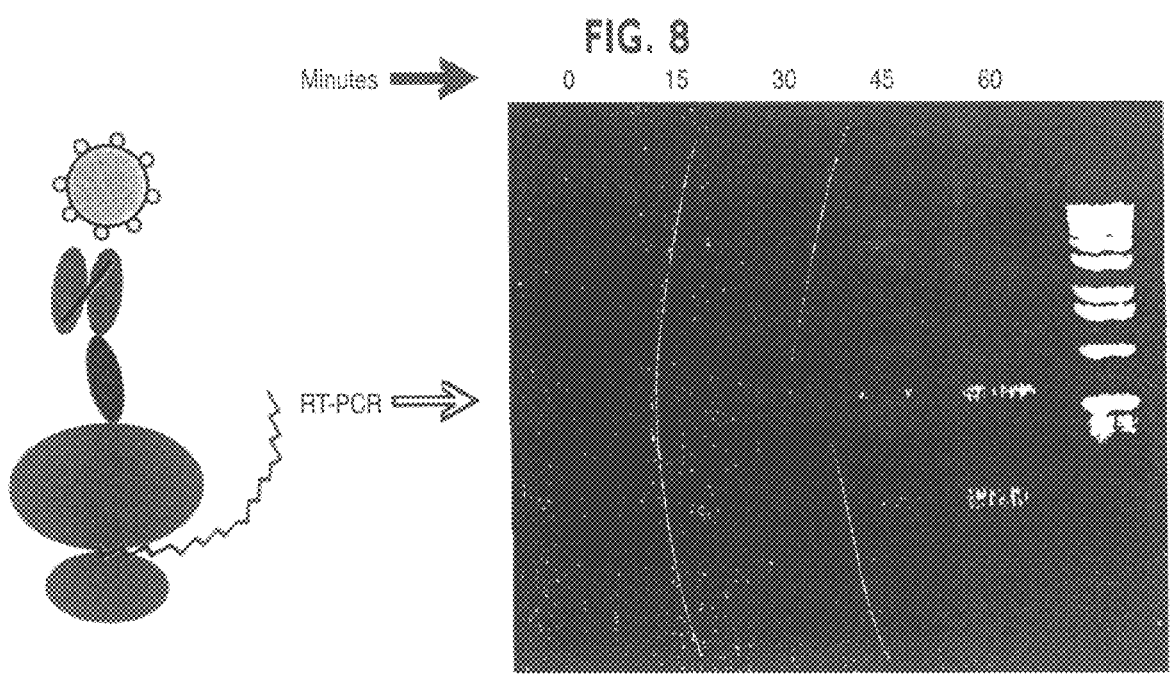

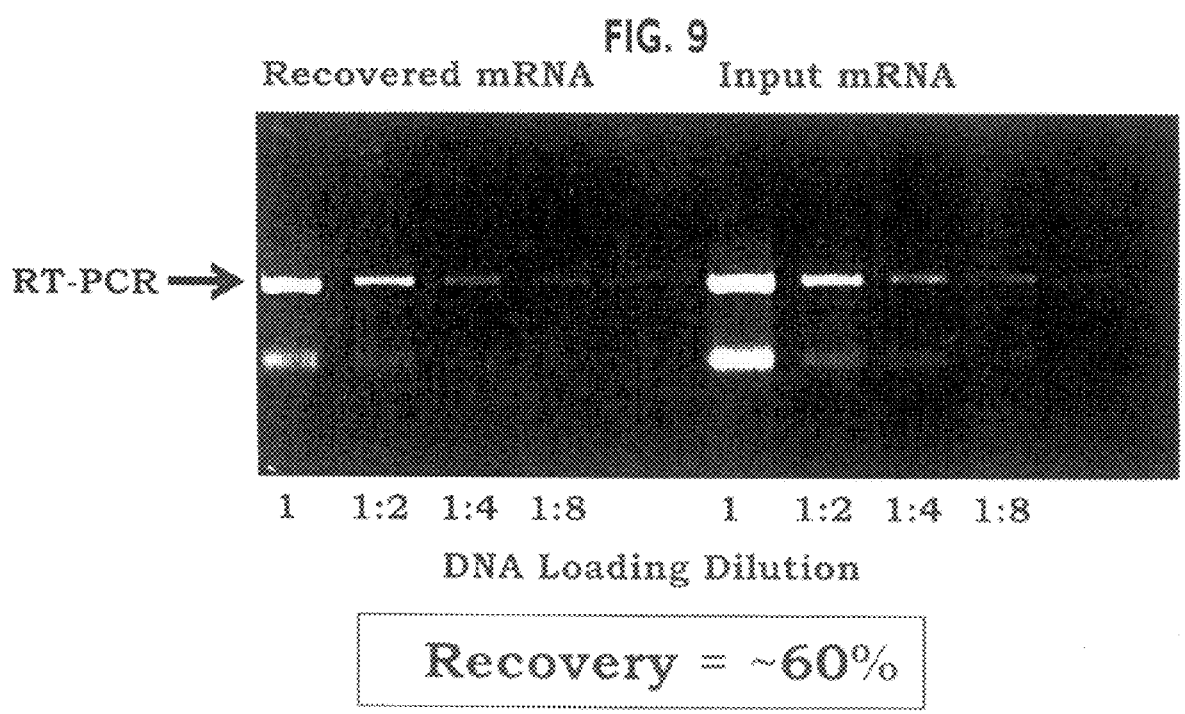

FIG. 12

ARM SELECTION: ERROR RATE IN ONE CYCLE

```
DB3 : QSGPELKKPGETVKISCKASGYAFKNYGVNWVKEAPGKDLKWMGWINIYT
(1)   QSGPELKKPGETVTISCKASGFAFKNYGANWVKEAPGKDLKWMGWIYIYS
(2)   QSGPELKKPGETVKISCKASGYAFKNYGVNWVKEAPGKDLKWMGWINIYS
(3)   QSGPELKKPGETVKISCKASGYAFKNYGVNWVKEAPGKDLKWMGWINIYT
(4)   QSGPELKKPGETVKISCKASGYAFKNYGANWVKEAPGKDLKWMGWINIYT
(5)   QSGPELKKPGETVKISCKASGYAFKNYGVNWVKGAPGKDLKWMGWINIYT
(6)   QSGPELKKPGETVKISCKASGYAFKNYGVNWVKEAPGKDLKWMGWINIYT

DB3 : GEPTYVDDFKGRFAFSLETSASTAYLEINNLKNEDTATYFCTRGD
(1)   GEPTFVDDFKGRFAFSLETSAS....
(2)   GEPTYVDDFKGRFAFSLETSASTAYLEITYLKNEDTATYFCTRSD
(3)   GEPTYVDDFKGRFAFSLETSASTAYLEINNLKNEDTATYFCTRSD
(4)   GEPTYVDDFKGRFAFSLETSASTAYLEINNLKNEDTATYFCTRSD
(5)   GEPTYVDDFKGRFAFSLETSASTAYLEINNLKNEDTATYFCTRGD
(6)   GEPTYVDDFKGRFAFSLETSASTAYLEI??LKNEDTATFFCTRGD
```

Nucleotide error: 9/1682 = 0.54%

FIG. 13
Ratio
DB3$^R$ : DB3$^{H35}$
1 : 10
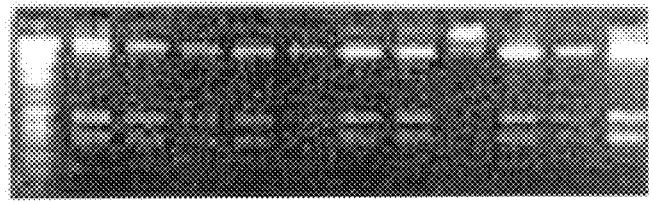
1 : 10$^2$
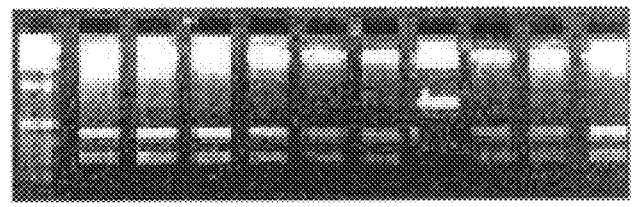
1 : 10$^3$
1 : 10$^4$
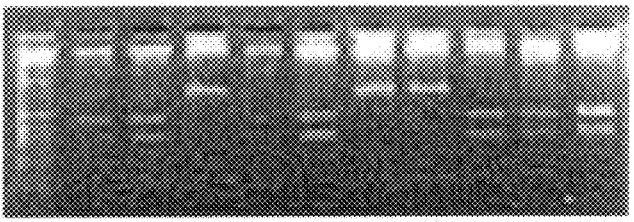
1 : 10$^5$
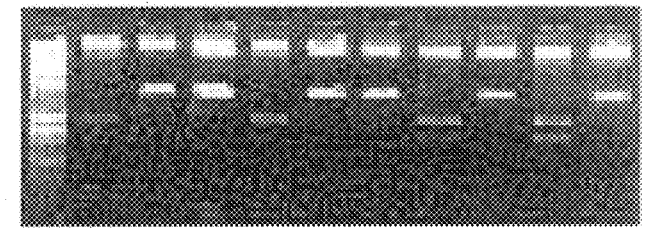

H3 Sequence

DB3R:    GDYVNRYFDVW

Library: GDTR*VW

Mut:     GD TRR SQK VW

FIG. 19

Sequences of human antibody V regions selected by ARM display

VH sequences

| Clone | VH gene | CDR H1 | CDRH2 | CDR H3 | |
|---|---|---|---|---|---|
| | | 31 | 50 | 95 | |
| 1578/P5 | 4 | SYYWS | WIGRIYTSDSTNYNPSLKS | AITGTAFDI | [SEQ ID 15, 16, 17] |
| 1578/P6 | 4 | SYYWS | WIGRIYTSGSTNYNPSLKG | DSDWNYPFDY | [SEQ ID 15, 18, 19] |
| 1578/P1 | 1-2 | GYYMH | WINPNSGGTNYAQKFQG | YPLLTGDGAFDI | [SEQ ID 20, 21, 22] |
| 1578/P2 | 1-2 | GYYMH | WINPNSGGTNYAQKFQG | DDYEIDWYFGL | [SEQ ID 20, 21, 23] |
| 1578/P9 | 1-2 | GYYMH | WINPNSGGTNYAQKFQG | DLSTEDQAFDI | [SEQ ID 20, 21, 24] |
| 1578/P10 | 1-2 | GYYMH | WINPN??GTNY?QKFQG | DLGNWFDP | [SEQ ID 20, 21, 26] |
| 1578/P11 | 1-2 | GYYMH | WINPNSGGTNY?QKFQG | GSDYGDYEYFQH | [SEQ ID 20, 21, 27] |
| 1578/P14 | 1-2 | GYYMH | WINPNSGGTNYAQKFQG | GSSYGDYEY?QH | [SEQ ID 20, 21, 28] |
| 1578/P16 | 1-2 | GYYMH | WINPNSGGTNYAQKFQG | EYNWFDP | [SEQ ID 20, 21, 29] |
| 1578/t4 | 1-2 | GYYMH | WINPNSGGTNYAQKFQG | QYYDFWSGYYYFDY | [SEQ ID 20, 21, 30] |

VL Sequences

| Clone | VL gene | CDR L1 | CDRL2 | CDR L3 | |
|---|---|---|---|---|---|
| 1578/P5 | 1-12 | RASQGISRWLA | AGSSLQ | | [SEQ ID 21,32] |
| 1578/P6 | 1-12 | RASQGISSWLA | AASSLQ | | [SEQ ID 33,34] |
| 1578/P1 | 4-01 | SQSVLYSFS?KNYL | ASTRES | | [SEQ ID 35, 36] |
| 1578/P2 | 4-01 | SQSVLYSFSNNKNYL | AFTREG | | [SEQ ID 37, 38] |
| 1578/t4 | 4-01 | SQSGLYSFNNKNYL | | | [SEQ ID 39] | p= anti-progesterone
t= anti-testosterone 1  2  3  4  5  6  7

SEQUENCE LISTING

```
<160> NUMBER OF SEQ ID NOS: 54

<210> SEQ ID NO 1
<211> LENGTH: 1101
<212> TYPE: DNA
<213> ORGANISM: Artificial Sequence
<220> FEATURE:
<223> OTHER INFORMATION: DB3 VH/K expression construct used in ARM
      generation

<400> SEQUENCE: 1
gcgcgaatac gactcactat agagggacaa accatgsagg tcmarctcga gsagtcwgga      60
cctgagctga agaagcctgg agagacagtc aagatctcct gcaaggcttc tgggtatgcc     120
ttcaaaaact atggagtgaa ctgggtgaag gaggctccag gaaaggattt aaagtggatg     180
ggctggataa acatctacac tggggagcca acatatgttg atgacttcaa gggacggttt     240
gccttctctt tggaaacctc tgccagcact gcctatttgg agatcaacaa cctcaaaaat     300
gaagacacgg caacgtattt ctgtacaaga ggtgactacg tcaactggta cttcgatgtc     360
```

```
tggggcgcag ggaccacggt caccgtctcc tcagccaaaa cgacacccccc atctgtctat      420 ccactggccg agctcgtgat gacccagatt ccactctccc tgcctgtcaa tcttggagat      480
caagcctcca tctcttgcag atctagtcag agccttgtac acagtaatgg aaacacctat      540
ttacattggt acctgcagaa gccaggccag tctccaaagc tcctgatcta caaagtttcc      600
aaccgatttt atgggtccc agacaggttc agtggcagtg atcagggac agatttcaca        660 ctcaagatca gcagagtgga ggctgaggat ctgggaattt atttctgctc tcaaagttca      720
catgttcctc cgacgttcgg tggaggcacc aagctggaat caaacgggc tgatgctgca       780 ccaactgtat ccatcttccc accatccagt gagcagttaa catctggagg tgcctcagtc      840
gtgtgcttct tgaacaactt ctaccccaaa gacatcaatg tcaagtggaa aattgatggc      900
agtgaacgac aaaatggcgt cctgaacagt tggactgatc aggacagcaa agacagcacc      960
tacagcatga gcagcaccct cacgttgacc aaggacgagt atgaacgaca taacagctat     1020
acctgtgagg ccactcacaa gacatcaact tcacccattg tcaagagctt caacaggaat     1080
gagtgtggtg gatccagtgc a                                                1101

<210> SEQ ID NO 2
<211> LENGTH: 1103
<212> TYPE: DNA
<213> ORGANISM: Artificial Sequence
<220> FEATURE:
<223> OTHER INFORMATION: Primers used in the modified ARM display cycle

<400> SEQUENCE: 2
gcagctaata cgactcacta taggaacaga ccaccatgsa ggtcmarctc gagsagtcwg       60
gacctgagct gaagaagcct ggagagacag tcaagatctc ctgcaaggct tctgggtatg     120
ccttcaaaaa ctatggagtg aactgggtga aggaggctcc aggaaaggat ttaaagtgga     180
tgggctggat aaacatctac actggggagc caacatatgt tgatgacttc aagggacggt     240
ttgccttctc tttggaaacc tctgccagca ctgcctattt ggagatcaac aacctcaaaa     300
atgaagacac ggcaacgtat ttctgtacaa gaggtgacta cgtcaaccgt tacttcgatg     360 tctgggcgc agggaccacg gtcaccgtct cctcagccaa aacgacaccc ccatctgtct      420
atccactggc cgagctcgtg atgacccaga ttccactctc cctgcctgtc aatcttggag     480
atcaagcctc catctcttgc agatctagtc agagccttgt acacagtaat ggaaacacct     540
atttacattg gtacctgcag aagccaggcc agtctccaaa gctcctgatc tacaaagttt     600
ccaaccgatt ttatgggtc ccagacaggt tcagtggcag tggatcaggg acagatttca     660
cactcaagat cagcagagtg gaggctgagg atctgggaat ttatttctgc tctcaaagtt     720
cacatgttcc tccgacgttc ggtggaggca ccaagctgga attcaaacgg gctgatgctg     780
caccaactgt atccatcttc ccaccatcca gtgagcagtt aacatctgga ggtgcctcag     840
tcgtgtgctt cttgaacaac ttctacccca agacatcaa tgtcaagtgg aaaattgatg      900
gcagtgaacg acaaaatggc gtcctgaaca gttggactga tcaggacagc aaagacagca     960
cctacagcat gagcagcacc ctcacgttga ccaaggacga gtatgaacga cataacagct    1020 ataccctgtga ggccactcac aagacatcaa cttcacccat tgtcaagagc ttcaacagga    1080
atgagtgtgg tggatccagt gca                                             1103

<210> SEQ ID NO 3
<211> LENGTH: 59
<212> TYPE: DNA
```

```
<213> ORGANISM: Artificial Sequence
<220> FEATURE:
<223> OTHER INFORMATION: Primer

<400> SEQUENCE: 3
gcgcgaatac gactcactat agagggacaa accatgsagg tcmarctcga gsagtcwgg        59

<210> SEQ ID NO 4
<211> LENGTH: 36
<212> TYPE: DNA
<213> ORGANISM: Artificial Sequence
<220> FEATURE:
<223> OTHER INFORMATION: Primer

<400> SEQUENCE: 4
tgcactggat ccaccacact cattcctgtt gaagct                                 36

<210> SEQ ID NO 5
<211> LENGTH: 61
<212> TYPE: DNA
<213> ORGANISM: Artificial Sequence
<220> FEATURE:
<223> OTHER INFORMATION: Primer

<400> SEQUENCE: 5
gcagctaata cgactcacta taggaacaga ccaccatgsa ggtcmarctc gagsagtcwg        60
g                                                                       61

<210> SEQ ID NO 6
<211> LENGTH: 61
<212> TYPE: DNA
<213> ORGANISM: Artificial Sequence
<220> FEATURE:
<223> OTHER INFORMATION: Primer

<400> SEQUENCE: 6
gcagctaata cgactcacta taggaacaga ccaccatgsa ggtmcasctc gagsagtctg        60
g                                                                       61

<210> SEQ ID NO 7
<211> LENGTH: 29
<212> TYPE: DNA
<213> ORGANISM: Artificial Sequence
<220> FEATURE:
<223> OTHER INFORMATION: Primer

<400> SEQUENCE: 7
gctctagaac actttcccct gttgaagct                                         29

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
gctctagagc tcagcgtcag ggtgctgct                                         29

<210> SEQ ID NO 9
<211> LENGTH: 26
<212> TYPE: DNA
<213> ORGANISM: Artificial Sequence
<220> FEATURE:
<223> OTHER INFORMATION: Primer
```

```
<400> SEQUENCE: 9
gctctagaga agacagatgg tgcagc                                           26

<210> SEQ ID NO 10
<211> LENGTH: 83
<212> TYPE: DNA
<213> ORGANISM: Artificial Sequence
<220> FEATURE:
<223> OTHER INFORMATION: Primer

<400> SEQUENCE: 10
cggaattctc tagagtgatg gtgatggtga tggtagactt tgtgtttctc gtagtctgct     60
ttgctcagcg tcagggtgct gct                                             83

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
ggggtagaag ttgttcaaga ag                                              22

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
ctggatggtg ggaagatgg                                                  19

<210> SEQ ID NO 13
<211> LENGTH: 74
<212> TYPE: DNA
<213> ORGANISM: Artificial Sequence
<220> FEATURE:
<223> OTHER INFORMATION: Primer

<400> SEQUENCE: 13
gctctagagg cctcacaggt atagctgtta tgtcgttcat actcgtcctt ggtcaacgtg     60
agggtgctgc tcat                                                       74

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
cgtgagggtg ctgctcatg                                                  19

<210> SEQ ID NO 15
<211> LENGTH: 5
<212> TYPE: PRT
<213> ORGANISM: Homo sapiens

<400> SEQUENCE: 15

Ser Tyr Tyr Trp Ser
1               5
```

<210> SEQ ID NO 16
<211> LENGTH: 19
<212> TYPE: PRT
<213> ORGANISM: Homo sapiens

<400> SEQUENCE: 16

Trp Ile Gly Arg Ile Tyr Thr Ser Asp Ser Thr Asn Tyr Asn Pro Ser
1               5                   10                  15

Leu Lys Ser

<210> SEQ ID NO 17
<211> LENGTH: 9
<212> TYPE: PRT
<213> ORGANISM: Homo sapiens

<400> SEQUENCE: 17

Ala Ile Thr Gly Thr Ala Phe Asp Ile
1               5

<210> SEQ ID NO 18
<211> LENGTH: 19
<212> TYPE: PRT
<213> ORGANISM: Homo sapiens

<400> SEQUENCE: 18

Trp Ile Gly Arg Ile Tyr Thr Ser Gly Ser Thr Asn Tyr Asn Pro Ser
1               5                   10                  15

Leu Lys Gly

<210> SEQ ID NO 19
<211> LENGTH: 10
<212> TYPE: PRT
<213> ORGANISM: Homo sapiens

<400> SEQUENCE: 19

Asp Ser Asp Trp Asn Tyr Pro Phe Asp Tyr
1               5                   10

<210> SEQ ID NO 20
<211> LENGTH: 5
<212> TYPE: PRT
<213> ORGANISM: Homo sapiens

<400> SEQUENCE: 20

Gly Tyr Tyr Met His
1               5

<210> SEQ ID NO 21
<211> LENGTH: 17
<212> TYPE: PRT
<213> ORGANISM: Homo sapiens

<400> SEQUENCE: 21

Trp Ile Asn Pro Asn Ser Gly Gly Thr Asn Tyr Ala Gln Lys Phe Gln
1               5                   10                  15

Gly

<210> SEQ ID NO 22
<211> LENGTH: 12
<212> TYPE: PRT
<213> ORGANISM: Homo sapiens

```
<400> SEQUENCE: 22

Tyr Pro Leu Leu Thr Gly Asp Gly Ala Phe Asp Ile
1               5                   10

<210> SEQ ID NO 23
<211> LENGTH: 11
<212> TYPE: PRT
<213> ORGANISM: Homo sapiens

<400> SEQUENCE: 23

Asp Asp Tyr Glu Ile Asp Trp Tyr Phe Gly Leu
1               5                   10

<210> SEQ ID NO 24
<211> LENGTH: 11
<212> TYPE: PRT
<213> ORGANISM: Homo sapiens

<400> SEQUENCE: 24

Asp Leu Ser Thr Glu Asp Gln Ala Phe Asp Ile
1               5                   10

<210> SEQ ID NO 25
<211> LENGTH: 17
<212> TYPE: PRT
<213> ORGANISM: Homo sapiens
<220> FEATURE:
<221> NAME/KEY: UNSURE
<222> LOCATION: (6)..(7)
<223> OTHER INFORMATION: Xaa is unknown
<221> NAME/KEY: UNSURE
<222> LOCATION: (12)..(12)
<223> OTHER INFORMATION: Xaa is unknown

<400> SEQUENCE: 25

Trp Ile Asn Pro Asn Xaa Xaa Gly Thr Asn Tyr Xaa Gln Lys Phe Gln
1               5                   10                  15

Gly

<210> SEQ ID NO 26
<211> LENGTH: 8
<212> TYPE: PRT
<213> ORGANISM: Homo sapiens

<400> SEQUENCE: 26

Asp Leu Gly Asn Trp Phe Asp Pro
1               5

<210> SEQ ID NO 27
<211> LENGTH: 12
<212> TYPE: PRT
<213> ORGANISM: Homo sapiens

<400> SEQUENCE: 27

Gly Ser Asp Tyr Gly Asp Tyr Glu Tyr Phe Gln His
1               5                   10

<210> SEQ ID NO 28
<211> LENGTH: 12
<212> TYPE: PRT
<213> ORGANISM: Homo sapiens
<220> FEATURE:
<221> NAME/KEY: UNSURE
<222> LOCATION: (10)..(10)
<223> OTHER INFORMATION: Xaa is unknown
```

```
<400> SEQUENCE: 28

Gly Ser Ser Tyr Gly Asp Tyr Glu Tyr Xaa Gln His
1               5                   10

<210> SEQ ID NO 29
<211> LENGTH: 7
<212> TYPE: PRT
<213> ORGANISM: Homo sapiens

<400> SEQUENCE: 29

Glu Tyr Asn Trp Phe Asp Pro
1               5

<210> SEQ ID NO 30
<211> LENGTH: 14
<212> TYPE: PRT
<213> ORGANISM: Homo sapiens

<400> SEQUENCE: 30

Gln Tyr Tyr Asp Phe Trp Ser Gly Tyr Tyr Phe Asp Tyr
1               5                   10

<210> SEQ ID NO 31
<211> LENGTH: 11
<212> TYPE: PRT
<213> ORGANISM: Homo sapiens

<400> SEQUENCE: 31

Arg Ala Ser Gln Gly Ile Ser Arg Trp Leu Ala
1               5                   10

<210> SEQ ID NO 32
<211> LENGTH: 6
<212> TYPE: PRT
<213> ORGANISM: Homo sapiens

<400> SEQUENCE: 32

Ala Gly Ser Ser Leu Gln
1               5

<210> SEQ ID NO 33
<211> LENGTH: 11
<212> TYPE: PRT
<213> ORGANISM: Homo sapiens

<400> SEQUENCE: 33

Arg Ala Ser Gln Gly Ile Ser Ser Trp Leu Ala
1               5                   10

<210> SEQ ID NO 34
<211> LENGTH: 6
<212> TYPE: PRT
<213> ORGANISM: Homo sapiens

<400> SEQUENCE: 34

Ala Ala Ser Ser Leu Gln
1               5

<210> SEQ ID NO 35
<211> LENGTH: 14
<212> TYPE: PRT
<213> ORGANISM: Homo sapiens
<220> FEATURE:
<221> NAME/KEY: UNSURE
<222> LOCATION: (10)..(10)
```

```
<223> OTHER INFORMATION: Xaa is unknown

<400> SEQUENCE: 35

Ser Gln Ser Val Leu Tyr Ser Phe Ser Xaa Lys Asn Tyr Leu
1               5                   10

<210> SEQ ID NO 36
<211> LENGTH: 6
<212> TYPE: PRT
<213> ORGANISM: Homo sapiens

<400> SEQUENCE: 36

Ala Ser Thr Arg Glu Ser
1               5

<210> SEQ ID NO 37
<211> LENGTH: 15
<212> TYPE: PRT
<213> ORGANISM: Homo sapiens

<400> SEQUENCE: 37

Ser Gln Ser Val Leu Tyr Ser Phe Ser Asn Asn Lys Asn Tyr Leu
1               5                   10                  15

<210> SEQ ID NO 38
<211> LENGTH: 6
<212> TYPE: PRT
<213> ORGANISM: Homo sapiens

<400> SEQUENCE: 38

Ala Phe Thr Arg Glu Gly
1               5

<210> SEQ ID NO 39
<211> LENGTH: 14
<212> TYPE: PRT
<213> ORGANISM: Homo sapiens

<400> SEQUENCE: 39

Ser Gln Ser Gly Leu Tyr Ser Phe Asn Asn Lys Asn Tyr Leu
1               5                   10

<210> SEQ ID NO 40
<211> LENGTH: 50
<212> TYPE: PRT
<213> ORGANISM: Artificial Sequence
<220> FEATURE:
<223> OTHER INFORMATION: DB3 VH/K ARM

<400> SEQUENCE: 40

Gln Ser Gly Pro Glu Leu Lys Lys Pro Gly Glu Thr Val Lys Ile Ser
1               5                   10                  15

Cys Lys Ala Ser Gly Tyr Ala Phe Lys Asn Tyr Gly Val Asn Trp Val
                20                  25                  30

Lys Glu Ala Pro Gly Lys Asp Leu Lys Trp Met Gly Trp Ile Asn Ile
            35                  40                  45

Tyr Thr
    50

<210> SEQ ID NO 41
<211> LENGTH: 50
<212> TYPE: PRT
<213> ORGANISM: Artificial Sequence
<220> FEATURE:
```

-continued

<223> OTHER INFORMATION: Clone of DB3

<400> SEQUENCE: 41

Gln Ser Gly Pro Glu Leu Lys Lys Pro Gly Glu Thr Val Thr Ile Ser
1               5                   10                  15

Cys Lys Ala Ser Gly Phe Ala Phe Lys Asn Tyr Gly Ala Asn Trp Val
            20                  25                  30

Lys Glu Ala Pro Gly Lys Asp Leu Lys Trp Met Gly Trp Ile Tyr Ile
        35                  40                  45

Tyr Ser
    50

<210> SEQ ID NO 42
<211> LENGTH: 50
<212> TYPE: PRT
<213> ORGANISM: Artificial Sequence
<220> FEATURE:
<223> OTHER INFORMATION: Clone of DB3

<400> SEQUENCE: 42

Gln Ser Gly Pro Glu Leu Lys Lys Pro Gly Glu Thr Val Lys Ile Ser
1               5                   10                  15

Cys Lys Ala Ser Gly Tyr Ala Phe Lys Asn Tyr Gly Val Asn Trp Val
            20                  25                  30

Lys Glu Ala Pro Gly Lys Asp Leu Lys Trp Met Gly Trp Ile Asn Ile
        35                  40                  45

Tyr Ser
    50

<210> SEQ ID NO 43
<211> LENGTH: 50
<212> TYPE: PRT
<213> ORGANISM: Artificial Sequence
<220> FEATURE:
<223> OTHER INFORMATION: Clone of DB3

<400> SEQUENCE: 43

Gln Ser Gly Pro Glu Leu Lys Lys Pro Gly Glu Thr Val Lys Ile Ser
1               5                   10                  15

Cys Lys Ala Ser Gly Tyr Ala Phe Lys Asn Tyr Gly Val Asn Trp Val
            20                  25                  30

Lys Glu Ala Pro Gly Lys Asp Leu Lys Trp Met Gly Trp Ile Asn Ile
        35                  40                  45

Tyr Thr
    50

<210> SEQ ID NO 44
<211> LENGTH: 50
<212> TYPE: PRT
<213> ORGANISM: Artificial Sequence
<220> FEATURE:
<223> OTHER INFORMATION: Clone of DB3

<400> SEQUENCE: 44

Gln Ser Gly Pro Glu Leu Lys Lys Pro Gly Glu Thr Val Lys Ile Ser
1               5                   10                  15

Cys Lys Ala Ser Gly Tyr Ala Phe Lys Asn Tyr Gly Ala Asn Trp Val
            20                  25                  30

Lys Glu Ala Pro Gly Lys Asp Leu Lys Trp Met Gly Trp Ile Asn Ile
        35                  40                  45

Tyr Thr
    50

<210> SEQ ID NO 45
<211> LENGTH: 50
<212> TYPE: PRT
<213> ORGANISM: Artificial Sequence
<220> FEATURE:
<223> OTHER INFORMATION: Clone of DB3

<400> SEQUENCE: 45

Gln Ser Gly Pro Glu Leu Lys Lys Pro Gly Glu Thr Val Lys Ile Ser
1               5                   10                  15

Cys Lys Ala Ser Gly Tyr Ala Phe Lys Asn Tyr Gly Val Asn Trp Val
            20                  25                  30

Lys Gly Ala Pro Gly Lys Asp Leu Lys Trp Met Gly Trp Ile Asn Ile
        35                  40                  45

Tyr Thr
    50

<210> SEQ ID NO 46
<211> LENGTH: 50
<212> TYPE: PRT
<213> ORGANISM: Artificial Sequence
<220> FEATURE:
<223> OTHER INFORMATION: Clone of DB3

<400> SEQUENCE: 46

Gln Ser Gly Pro Glu Leu Lys Lys Pro Gly Glu Thr Val Lys Ile Ser
1               5                   10                  15

Cys Lys Ala Ser Gly Tyr Ala Phe Lys Asn Tyr Gly Val Asn Trp Val
            20                  25                  30

Lys Glu Ala Pro Gly Lys Asp Leu Lys Trp Met Gly Trp Ile Asn Ile
        35                  40                  45

Tyr Thr
    50

<210> SEQ ID NO 47
<211> LENGTH: 45
<212> TYPE: PRT
<213> ORGANISM: Artificial Sequence
<220> FEATURE:
<223> OTHER INFORMATION: DB3 VH/K ARM

<400> SEQUENCE: 47

Gly Glu Pro Thr Tyr Val Asp Asp Phe Lys Gly Arg Phe Ala Phe Ser
1               5                   10                  15

Leu Glu Thr Ser Ala Ser Thr Ala Tyr Leu Glu Ile Asn Asn Leu Lys
            20                  25                  30

Asn Glu Asp Thr Ala Thr Tyr Phe Cys Thr Arg Gly Asp
        35                  40                  45

<210> SEQ ID NO 48
<211> LENGTH: 45
<212> TYPE: PRT
<213> ORGANISM: Artificial Sequence
<220> FEATURE:
<223> OTHER INFORMATION: Clone of DB3

<400> SEQUENCE: 48

Gly Glu Pro Thr Phe Val Asp Asp Phe Lys Gly Arg Phe Ala Phe Ser
1               5                   10                  15

Leu Glu Thr Ser Ala Ser Thr Ala Tyr Leu Glu Ile Asn Asn Leu Lys
            20                  25                  30

Asn Glu Asp Thr Ala Thr Tyr Phe Cys Thr Arg Gly Asp
            35                  40                  45

<210> SEQ ID NO 49
<211> LENGTH: 45
<212> TYPE: PRT
<213> ORGANISM: Artificial Sequence
<220> FEATURE:
<223> OTHER INFORMATION: Clone of DB3

<400> SEQUENCE: 49

Gly Glu Pro Thr Tyr Val Asp Asp Phe Lys Gly Arg Phe Ala Phe Ser
1               5                   10                  15

Leu Glu Thr Ser Ala Ser Thr Ala Tyr Leu Glu Ile Thr Tyr Leu Lys
            20                  25                  30

Asn Glu Asp Thr Ala Thr Tyr Phe Cys Thr Arg Gly Asp
            35                  40                  45

<210> SEQ ID NO 50
<211> LENGTH: 45
<212> TYPE: PRT
<213> ORGANISM: Artificial Sequence
<220> FEATURE:
<223> OTHER INFORMATION: Clone of DB3

<400> SEQUENCE: 50

Gly Glu Pro Thr Tyr Val Asp Asp Phe Lys Gly Arg Phe Ala Phe Ser
1               5                   10                  15

Leu Glu Thr Ser Ala Ser Thr Ala Tyr Leu Glu Ile Asn Asn Leu Lys
            20                  25                  30

Asn Glu Asp Thr Ala Thr Tyr Phe Cys Thr Arg Ser Asp
            35                  40                  45

<210> SEQ ID NO 51
<211> LENGTH: 45
<212> TYPE: PRT
<213> ORGANISM: Artificial Sequence
<220> FEATURE:
<223> OTHER INFORMATION: Clone of DB3

<400> SEQUENCE: 51

Gly Glu Pro Thr Tyr Val Asp Asp Phe Lys Gly Arg Phe Ala Phe Ser
1               5                   10                  15

Leu Glu Thr Ser Ala Ser Thr Ala Tyr Leu Glu Ile Asn Asn Leu Lys
            20                  25                  30

Asn Glu Asp Thr Ala Thr Tyr Phe Cys Thr Arg Gly Asp
            35                  40                  45

<210> SEQ ID NO 52
<211> LENGTH: 45
<212> TYPE: PRT
<213> ORGANISM: Artificial Sequence
<220> FEATURE:
<223> OTHER INFORMATION: Clone of DB3
<221> NAME/KEY: UNSURE
<222> LOCATION: (29)..(30)
<223> OTHER INFORMATION: Xaa is unknown

<400> SEQUENCE: 52

Gly Glu Pro Thr Tyr Val Asp Asp Phe Lys Gly Arg Phe Ala Phe Ser
1               5                   10                  15

```
-continued

Leu Glu Thr Ser Ala Ser Thr Ala Tyr Leu Glu Ile Xaa Xaa Leu Lys
            20                  25                  30

Asn Glu Asp Thr Ala Thr Phe Phe Cys Thr Arg Gly Asp
        35                  40                  45

<210> SEQ ID NO 53
<211> LENGTH: 11
<212> TYPE: PRT
<213> ORGANISM: Artificial Sequence
<220> FEATURE:
<223> OTHER INFORMATION: Clone derived by ARM display from the DB3 H-3
      mutant library

<400> SEQUENCE: 53

Gly Asp Tyr Val Asn Arg Tyr Phe Asp Val Trp
1               5                   10

<210> SEQ ID NO 54
<211> LENGTH: 11
<212> TYPE: PRT
<213> ORGANISM: Artificial Sequence
<220> FEATURE:
<223> OTHER INFORMATION: H3 region of mutated clone

<400> SEQUENCE: 54

Gly Asp Thr Arg Pro Arg Ser Gln Lys Val Trp
1               5                   10
```

RIBOSOME COMPLEXES AS SELECTION PARTICLES FOR IN VITRO DISPLAY AND EVOLUTION OF PROTEINS

This application is a 371 of PCT/GB98/01564 filed on May 28, 1998, the entirety of which is hereby incorporated by reference.

BACKGROUND TO THE INVENTION

A current focus of interest in molecular biology and biotechnology is in the display of large libraries of proteins and peptides and in means of searching them by affinity selection. The key to genetic exploitation of a selection method is a physical link between individual molecules of the library (phenotype) and the genetic information encoding them (genotype). A number of cell-based methods are available, such as on the surfaces of phages (1), bacteria (2) and animal viruses (3). Of these, the most widely used is phage display, in which proteins or peptides are expressed individually on the surface of phage as fusions to a coat protein, while the same phage particle carries the DNA encoding the protein or peptide. Selection of the phage is achieved through a specific binding reaction involving recognition of the protein or peptide, enabling the particular phage to be isolated and cloned and the DNA for the protein or peptide to be recovered and propagated or expressed.

A particularly desirable application of display technology is the selection of antibody combining sites from combinatorial libraries (4). Screening for high affinity antibodies to specific antigens has been widely carried out by phage display of antibody fragments (4). Combinations of the variable (V) regions of heavy (H) and light (L) chains are displayed on the phage surface and recombinant phage are selected by binding to immobilised antigen. Single-chain (sc) Fv fragments, in which the $V_H$ and $V_L$ domains are linked by a flexible linker peptide, have been widely used to construct such libraries. Another type of single chain antibody fragment is termed $V_H/K$, in which the $V_H$ domain is linked to the complete light chain, i.e. $V_H$-linker-$V_L$-$C_L$ (10). This has a number of advantages, including stability of expression in $E.$ $coli$ and the use of the $C_L$ domain as a spacer and as a tag in detection systems such as ELISA and Western blotting. Antibody $V_H$ and $V_L$ region genes are readily obtained by PCR and can be recombined at random to produce large libraries of fragments (21). Such libraries may be obtained from normal or immune B lymphocytes of any mammalian species or constructed artificially from cloned gene fragments with synthetic H-CDR3 regions (third complementarity determining region of the heavy chain) generated in vitro (22). Single chain antibody libraries are potentially of a size of >$10^{10}$ members. Libraries can also be generated by mutagenesis of cloned DNA fragments encoding specific $V_H/V_L$ combinations and screened for mutants having improved properties of affinity or specificity. Mutagenesis is carried out preferably on the CDR regions, and particularly on the highly variable H-CDR3, where the potential number of variants which could be constructed from a region of 10 amino acids is $20^{10}$ or $10^{13}$.

It is clear that for efficient antibody display it is necessary to have a means of producing and selecting from very large libraries. However, the size of the libraries which can potentially be produced exceeds by several orders of magnitude the ability of current technologies to display all the members. Thus, the generation of phage display libraries requires bacterial transformation with DNA, but the low efficiency of DNA uptake by bacteria means that a typical number of transformants which can be obtained is only $10^7$–$10^9$ per transformation. While large phage display repertoires can be created (17), they require many repeated electroporations since transformation cannot be scaled up, making the process tedious or impractical. In addition to the limitations of transformation there are additional factors which reduce library diversity generated with bacteria, e.g. certain antibody fragments may not be secreted, may be proteolysed or form inclusion bodies, leading to the absence of such binding sites from the final library. These considerations apply to all cell-based methods. Thus for libraries with $10^{10}$ or more members, only a small fraction of the potential library can be displayed and screened using current methodologies. As noted, the size of an antibody library generated either from animal or human B cells or artificially constructed can readily exceed $10^{10}$ members, while the number of possible peptide sequences encoding a 10 residue sequence is $10^{13}$.

In order to avoid these limitations, alternative display systems have been sought, in particular in vitro methods which avoid the problem of transformation in library production. One such method is the display of proteins or peptides in nascent form on the surface of ribosomes, such that a stable complex with the encoding mRNA is also formed; the complexes are selected with a ligand for the protein or peptide and the genetic information obtained by reverse transcription of the isolated mRNA. This is known as ribosome or polysome display. A description of such a method is to be found in two U.S. patents, granted to G. Kawasaki/Optein Inc. (16). Therein, semi-random nucleotide sequences (as in a library) are attached to an 'expression unit' and transcribed in vitro; the resulting mRNAs are translated in vitro such that polysomes are produced; polysomes are selected by binding to a substance of interest and then disrupted; the released mRNA is recovered and used to construct cDNA. Two critical parts of the method are the stalling of the ribosome to produce stable complexes, for which cycloheximide is used, and the recovery of the mRNA, for which the bound polysomes are disrupted to release mRNA and the mRNA is then separately recovered. The latter is an integral part of the method as described by Kawasaki and adopted by all others until now. Thus, section VII of the patents (16) deals with the disruption of the polysomes by removal of magnesium, etc; no other method for recovery of RNA or cDNA is suggested other than ribosomal disruption. In U.S. Pat. No. 5,643,768, claim 1 refers to translating mRNA in such a way as to maintain polysomes with polypeptide chains attached, then contacting to a substance of interest, and finally isolating mRNA from the polysomes of interest. In claim 2, cDNA is constructed subsequent to isolating mRNA from the polysomes that specifically bind to the substance of interest. This is reiterated in claim 15, wherein step (g) comprises disrupting said polysomes to release said mRNA and step (h) comprises recovering said mRNA, thereby isolating a nucleotide sequence which encodes a polypeptide of interest. Similarly, this is repeated again in claim 29 (e) . . . isolating mRNA from the polysomes that specifically react with the substance of interest. In U.S. Pat. No. 5,658,754, claim 1 (g) also requires disrupting said polysomes to release mRNA; (h) is recovering said mRNA; and (i) is constructing cDNA from said recovered mRNA. However, Kawasaki did not reduce the method to practice in these filings and provided no results. Accordingly, the method was not optimised and he was unaware of the inefficiency of the system as he described it, in particular that due to the method of recovery of mRNA by polysome disruption.

Another description of prokaryotic polysome display, this time reduced to practice, is the international published application WO 95/11922 by Affymax Technologies (18) and the associated publication of Mattheakis et al. (14). Both relate to affinity screening of polysomes displaying nascent peptides, while the patent filing also claims screening of antibody libraries similarly displayed on polysomes. They refer to libraries of polysomes, specifically generated in the *E. coli* S30 system in which transcription and translation are coupled. To produce a population of stalled polysomes, agents such as rifampicin or chloramphenicol, which block prokaryotic translation, are added. The means of recovering the genetic information following selection of stalled ribosomes is again by elution of the mRNA. In the flowsheet of the method shown in FIG. 10 of the patent application (18), an integral part is step 4, namely elution of mRNA from the ribosome complexes prior to cDNA synthesis. The main example in the patent and the publication is of screening a large peptide library with $10^{12}$ members by polysome display and selection of epitopes by a specific antibody. The polysomes were selected in antibody-coated microplate wells. The bound mRNA was liberated with an elution buffer containing 20 mM EDTA and was then phenol extracted and ethanol precipitated in the presence of glycogen and the pellet resuspended in $H_2O$.

It is clear that the procedures described by Mattheakis et al. are very inefficient at capturing and/or recovering mRNA; thus, on p.72 of the Affymax filing (18), only 1–2% of radiolabelled polysomal mRNA encoding the specific peptide epitope was recovered, which was acknowledged to be low (line 5). The patent application (but not the publication) also includes the selection of an antibody fragment, but with much less detail. In this case, Dynal magnetic beads coated with antigen were used as the affinity matrix. In the example, labelled mRNA was specifically recovered but they did not show recovery of cDNA by RT-PCR. Hence there was no estimation of efficiency or sensitivity, and no demonstration of selection from a library or enrichment.

In a more recent publication (15), Hanes and Pluckthun modified the method of Mattheakis et al. for display and selection of single chain antibody fragments. While retaining the concept, additional features were introduced to make the method more suited to display of whole proteins in the prokaryotic, *E. coli* S30 system. One innovation is the stalling of the ribosome through the absence of a stop codon, which normally signals release of the nascent protein. Once again, recovery of genetic material was by dissociation of the ribosome complexes with 10 mM EDTA and isolation of the mRNA by ethanol precipitation (or Rneasy kit) prior to reverse transcription. Separate transcription and translation steps were used, and it was stated that the coupled procedure has lower efficiency; however, no data was provided to this effect. A large input of mRNA was used in each cycle (10 μg).

Many additions were incorporated by Hanes and Pluckthun in order to improve the yield of mRNA after the polysome display cycle, which was initially as low as 0.001% (15). These included stem loop structures at the 5' and 3' ends of the mRNA, vanadyl ribonucleoside complexes as nuclease inhibitor (which also partially inhibit translation), protein disulphide isomerase PDI (which catalyses formation of disulphide bonds) and an anti-sense nucleotide (to inhibit ssrA RNA which in the prokaryotic system otherwises cause the release and degradation of proteins synthesised without a stop codon). The combination of anti-ssrA and PDI improved efficiency by 12-fold overall. However, the yield of mRNA at the end of the cycle, with all additions, was still only 0.2% of input mRNA, expressing the combined efficiency of all steps, including ligand binding (on microtiter wells), RNA release and amplification. Affymax have already described a yield of 2%, i.e. 10-fold higher, as low (cited above).

Hanes and Pluckthun also demonstrated recovery of a specific antibody from a mixture (of two) in which it is initially present at a ratio of $1:10^8$. This required 5 sequential repetitions of the cycle, i.e. using the DNA product of one cycle as the starting point of the next. In FIG. 4(A) of ref. 15, there is a considerable carry over of the nonselected polysomes, probably reflecting the method of selection or mRNA recovery. As a consequence, the enrichment factor is relatively low, about 100-fold per cycle.

A further recent ribosome display method was described by Roberts and Szostak (23), in which the nascent protein is caused to bind covalently to its mRNA through a puromycin link. In this system, selection is carried out on these protein-mRNA fusions after dissociation of the ribosome. It thus differs significantly from the other methods described here since it does not involve selection of protein-ribosome-mRNA particles. Its efficiency is only 20–40 fold.

BRIEF DESCRIPTION OF THE INVENTION

It is clear that the described prokaryotic methods of polysome display leave considerable scope for methodological improvement to increase efficiency of recovery of mRNA, sensitivity and selection. In the invention described herein, we have developed a novel, eukaryotic method of ribosome display and demonstrate its application to selection and mutation (evolution) of antibodies and to selection of other proteins from mRNA libraries. It could equally be applied to isolation of genes from cDNA libraries.

The invention provides a method of displaying nascent proteins or peptides as complexes with eukaryotic ribosomes and the mRNA encoding the protein or peptide following transcription and translation in vitro, of further selecting complexes carrying a particular nascent protein or peptide by means of binding to a ligand, antigen or antibody, and of subsequently recovering the genetic information encoding the protein or peptide from the selected ribosome complex by reverse transcription and polymerase chain reaction (RT-PCR). The RT-PCR recovery step is carried out directly on the intact ribosome complex, without prior dissociation to release the mRNA, thus contributing to maximal efficiency and sensitivity. The steps of display, selection and recovery can be repeated in consecutive cycles. The method is exemplified using single-chain antibody constructs as antibody-ribosome-mRNA complexes (ARMs). It is suitable for the construction of very large display libraries, e.g. comprising over $10^{12}$ complexes, and of efficiently recovering the DNA encoding individual proteins after affinity selection. We provide evidence of highly efficient enrichment, e.g. $10^4$–$10^5$-fold per cycle, and examples demonstrating its utility in the display and selection of single chain antibody fragments from libraries, antibody engineering, selection of human antibodies and selection of proteins from mRNA libraries.

In its application to antibody fragments, the method is shown in FIG. 1. In this form, the method is also termed 'ARM display', since the selection particles consist of antibody-ribosome-mRNA complexes. The antibody is in the form of the single-chain fragment $V_H$/K described above, but the method is in principle equally applicable to any single chain form, such as scFv. The method differs in a number of particulars from those described above, leading to greater than expected improvements in efficiency, sensitivity and enrichment. In principle, it is based on two experimental results: (i) single-chain antibodies are functionally produced in vitro in rabbit reticulocyte lysates (7) and (ii) in the absence of a stop codon, individual nascent proteins remain associated with their corresponding mRNA as stable ternary polypeptide ribosome-mRNA complexes in cell-free systems (8,9). We have applied these findings to a strategy for generating libraries of eukaryotic ARM complexes and have efficiently selected complexes carrying specific combining sites using antigen-coupled magnetic particles. Selection simultaneously captures the relevant genetic information as mRNA.

The coupled transcription/translation system used here is a rabbit reticulocyte extract (Promega) which provides efficient utilisation of DNA. In particular, it avoids the separate isolation of mRNA as described in ref. 15, which is costly in materials and time. The deletion of the stop codon from the encoding DNA is more productive as a means of stalling the ribosome than the use of inhibitors, because it ensures that all mRNA's are read to the 3' end, rather than being stopped at random points in the translation process. The stabilising effect of deletion of the stop codon can be explained by the requirement for release factors which recognise the stop codon and normally terminate translation by causing release of the nascent polypeptide chain (26). In the absence of the stop codon, the nascent chain remains bound to the ribosome and the mRNA. Where it is problematic to engineer stop codon deletion as in cDNA or mRNA libraries, an alternative method would be the use of suppressor tRNA (charged with an amino acid) which recognises and reads through the stop codon, thereby preventing the action of release factors (24). A further strategy of ribosome stalling would be the use of suppressor tRNA not charged by an amino acid.

In a novel step which introduces a significant difference from preceding methods, we show that cDNA can be generated and amplified by single-step reverse transcription-polymerase chain reaction (RT-PCR) on the ribosome-bound mRNA, thus avoiding completely the isolation and subsequent recovery of mRNA by procedures that are costly in terms of material and time. The success and efficiency of this step is surprising, since it is generally assumed that during translation several ribosomes attach to the same mRNA molecule, creating a polysome, and it was not known what effect the presence of several ribosomes in tandem on a single mRNA molecule would have on reverse transcription, where the RT enzyme must read the length of the mRNA. Thus, it is not known whether the enzyme might be able to pass through adjacent ribosomes, or cause their removal from the mRNA, or only function on mRNA molecules to which only one ribosome was attached. Whatever the explanation, this step contributes greatly to the demonstrated efficiency of the system, in which up to 60% of the input mRNA can be recovered in one cycle (Example 6, FIG. 9), compared with only 2% in the prokaryotic systems described by Mattheakis et al (14) and 0.2% by Hanes and Pluckthun (15). Furthermore, we have shown that, in the eukaryotic system, extraction of the mRNA from the ribosome complex is five times less effective as a recovery procedure than RT-PCR on the nondisrupted complex and that much of the mRNA remains bound to the ribosome even after EDTA extraction (Example 8, FIG. 11).

The enrichment of individual antibody fragments using ARM display libraries is also more efficient than described for prokaryotic display (15). We have performed experiments which show that mixtures in which the desired specific fragment is present at one part in $10^5$ can yield a binding fragment after one cycle, with an effective enrichment factor of $>10^4$ fold, and that cycles can be run sequentially to isolate rarer molecular species from very large libraries (Examples 10 and 11). This is 2–3 orders of magnitude more efficient per cycle than the results reported in the prokaryotic system (15).

Since the ARM libraries are generated wholly by in vitro techniques (PCR) and do not require bacterial transformation, their size is limited mainly by the numbers of ribosomes which can be brought into the reaction mixture ($\sim10^{14}$ per ml in the rabbit reticulocyte kit, according to manufacturer's information) and the amount of DNA which can be handled conveniently per reaction. Hence the production of large libraries becomes much easier than in the phage display method, where the limiting factor is bacterial transformation. An important application is in the selection of proteins from large libraries of mutants; the library can be generated through PCR mutation either randomly or in a site-directed fashion and mutants with required specificity selected by antigen-binding. We demonstrate the use of the ARM display procedure to select antibody ($V_H/K$) fragments with altered specificity from such libraries. This application to antibody engineering is shown in Example 12, in which the specificity of an anti-progesterone antibody is altered to testosterone binding by a combination of mutagenesis and selection. Such procedures may also be used to produce catalytic antibodies. The operation of the ARM cycle itself also introduces a low level of random mutation through the errors of PCR and we show that the rate of such errors is 0.54% per cycle (Example 9). This can lead to selection of improved properties of affinity and specificity, and is termed 'protein evolution' to indicate the development of novel proteins through a combination of mutation and selection (15). The eukaryotic ARM cycle is well suited to carrying out efficient protein evolution in vitro.

The present invention also provides a novel method for obtaining antibodies from libraries made from immunised mice, bypassing hybridoma technology. In particular, we show that it can be used to make human antibodies by employing a combination of transgenic mouse technology and ARM ribosome display. Mice are available in which transgenic loci encoding human heavy and light chain antibody genes are incoporated into the genomes, such mice giving rise to human antibodies when immunised (20). We provide herein an example in which human antibodies are derived in vitro by ARM display of a library prepared from the lymphocytes of such mice (Example 13). This provides a novel route to the derivation of human antibodies for therapeutic purposes.

The ribosome display method described herein is also applicable to any protein or peptide which, having been translated in vitro, remains bound to the ribosome and its encoding mRNA. As well as the examples showing the applicability of ARM display to antibodies, we also demonstrate this more general application through translation of an mRNA library obtained directly from normal tissues for selection of individual polypeptide chains (Example 14).

This version of ribosome display thus meets the need for a simple in vitro display system for proteins or peptides. It is capable of a very large library size, combined with ease and efficiency of selection and recovery of genetic information; it is also less demanding of special conditions, more sensitive and capable of greater levels of enrichment than methods described hitherto. The combination of a eukaryotic system with efficient mRNA recovery provides a system with a far greater efficiency than would have been predicted by those practiced in the art.

FIGURE LEGENDS

FIG. 1. The ARM (antibody-ribosome-mRNA) display cycle, showing the generation of an ARM library by mutagenesis of a single-chain antibody fragment ($V_H/K$) template, selection of a specific ARM complex by binding to antigen-coupled magnetic beads, and recovery of the genetic information by RT-PCR.

FIG. 2A. [SEQ ID 1]. Sequence of the DB3 $V_H/K$ expression construct used in ARM generation. The location of the primers is shown in bold italics. Start points of the $V_H$, $V_L$, Cκ domains and linker are indicated. D1–D4 are four downstream primers. D1 is used to make the full-length DB3 $V_H/K$ DNA as starting material for the ARM display cycle. D2, D3 and D4 are all recovery primers for use in the first, second and third cycles respectively, in conjunction with the T7 primer (see FIG. 3). These primers are suitable for all mouse antibodies with a κ light chain.

FIG. 2B. [SEQ ID 2]. Primers used in the modified ARM display cycle. The new upstream T7 primer, including the T7 promoter and protein initiation signal, provide an improved yield. This figure also shows the EVOU primer sequence with the XbaI site underlined. In the recovery phase of the ARM display, the combination of the upstream (T7) primer and both the D2 and EVOU downstream primers lead to recovery of near full length cDNA in each cycle (see FIG. 4). These primers are suitable for all mouse antibodies with a κ light chain.

Figure 3:
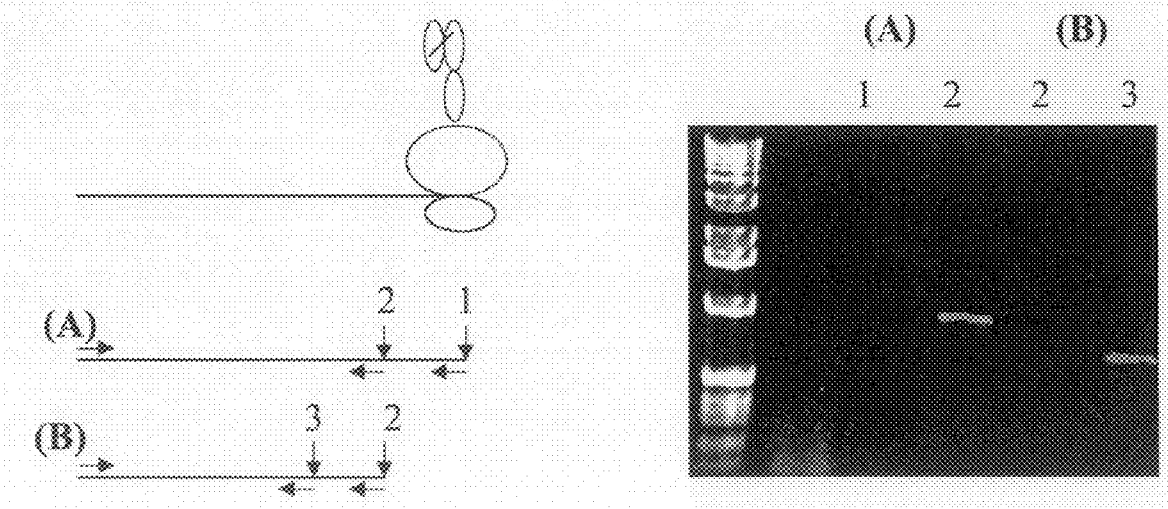

FIG. 3. Demonstration that the 3' end of the mRNA is hidden by the ribosome, and that recovery therefore requires the upstream primers D2 and D3 (FIG. 2A) for the recovery stages in cycles 1 and 2. In (A), full length DB3 VH/K was transcribed and either primer D1 (1) or D2 (2) used for recovery, which the gel shows was only successful for D2. In (B) the PCR product from cycle A was used in a second cycle with primers D2 (2) or D3 (3); now, the RT-PCR recovery was only successful with primer D3.

Figure 4:
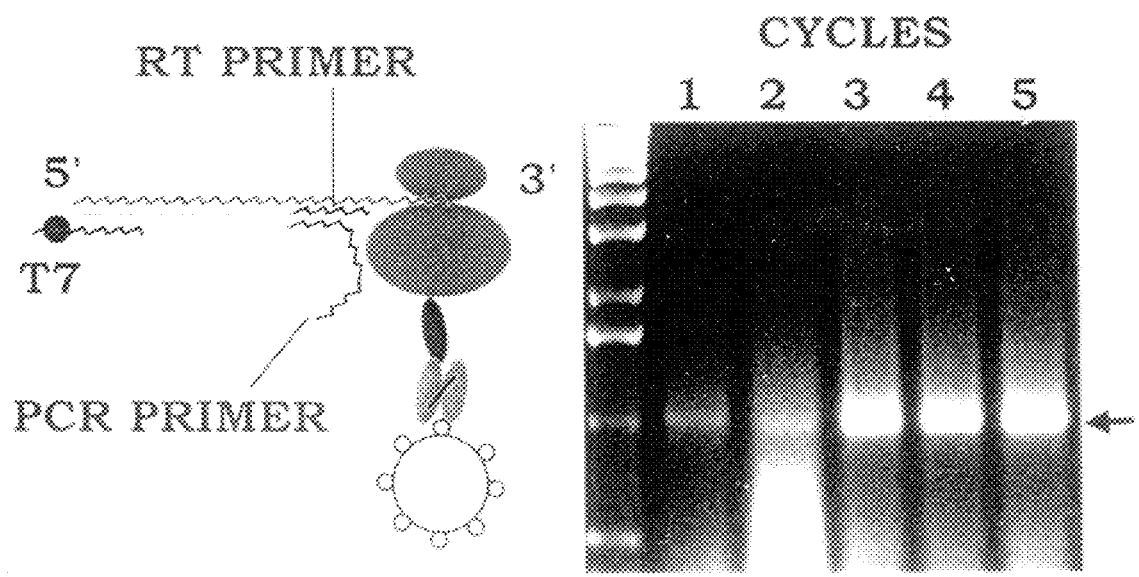

FIG. 4. Recovery of the same size $V_H/K$ DNA over 5 cycles using the 3-primer method. RT primer=D2 of FIG. 2B; PCR primer=EVOU of FIG. 2B.

Figure 5:
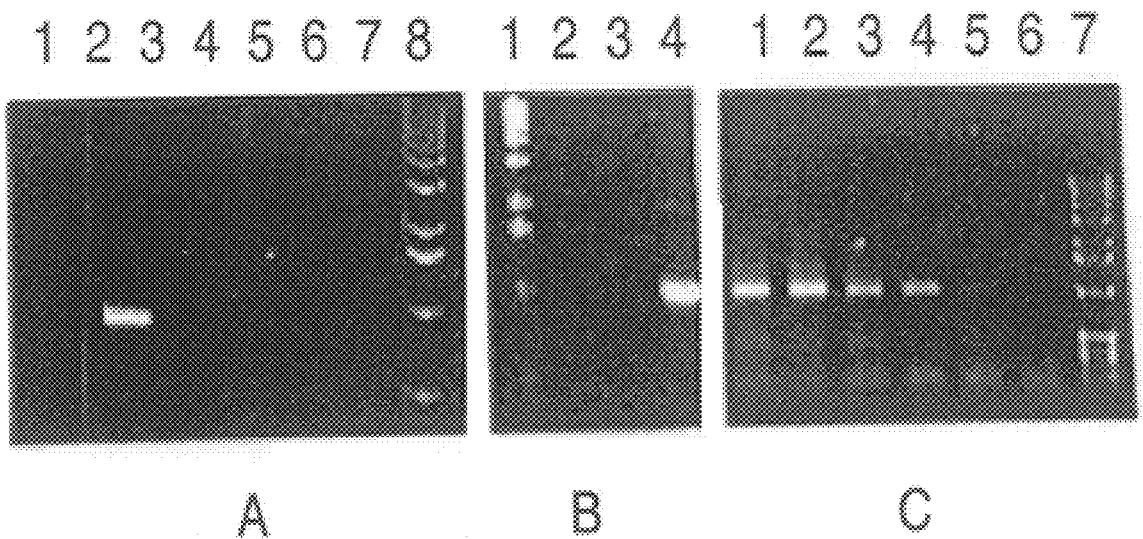

FIG. 5. Specific selection of an antibody $V_H/K$ fragment in the ARM cycle.
  A. Specific selection of $DB3^R$ ARM complexes by progesterone-BSA-coupled beads. Track 1, RT-PCR of nontranslated $DB3^R$ mRNA selected by progesterone-BSA beads; 2, RT-PCR of $DB3^R$ ARM selected by progesterone-BSA beads; 3, PCR of $DB3^R$ ARM selected by progesterone-BSA beads; 4, RT-PCR of $DB3^R$ ARM selected by testosterone-BSA beads; 5, PCR of $DB3^R$ ARM selected by testosterone-BSA beads; 6, RT-PCR of $DB3^R$ ARM selected by BSA beads; 7, PCR of $DB3^R$ ARMs selected by BSA beads. 8=1 kb DNA marker.
  B. Nonbinding of a $DB3^{H35}$ ARM library to progesterone-BSA-coupled beads. Track 1, 1 kb DNA marker; 2, RT-PCR of solution control; 3, RT-PCR of $DB3^{H35}$ ARMs selected by progesterone-BSA beads; 4, RT-PCR of $DB3^{H35}$ ARMs selected by rat anti-κ-coupled beads.
  C. Selection of $DB3^R$ from ARM libraries containing different ratios of $DB3^R$ and $DB3^{H35}$ mutants. Selection was with progesterone-BSA coupled beads. Track 1, ratio of $DB3^R$:$DB3^{H35}$ of 1:10; 2, 1:10$^2$; 3, 1:10$^3$; 4, 1:10$^4$; 5, 1:10$^5$; 6=$DB3^{H35}$ mutant library alone; 7, 1 kb DNA marker FIG. 6. Specific inhibition of the soluble DB3 $V_H/K$ fragment by free steroids in ELISA (right panel), and of DB3 $V_H/K$ in ARM format (centre), demonstrating the same specificity pattern. The centre panel shows the result at 100 ng/ml free steroid. This supports the correct folding of the antibody fragment on the ribosome.

Figure 6A:
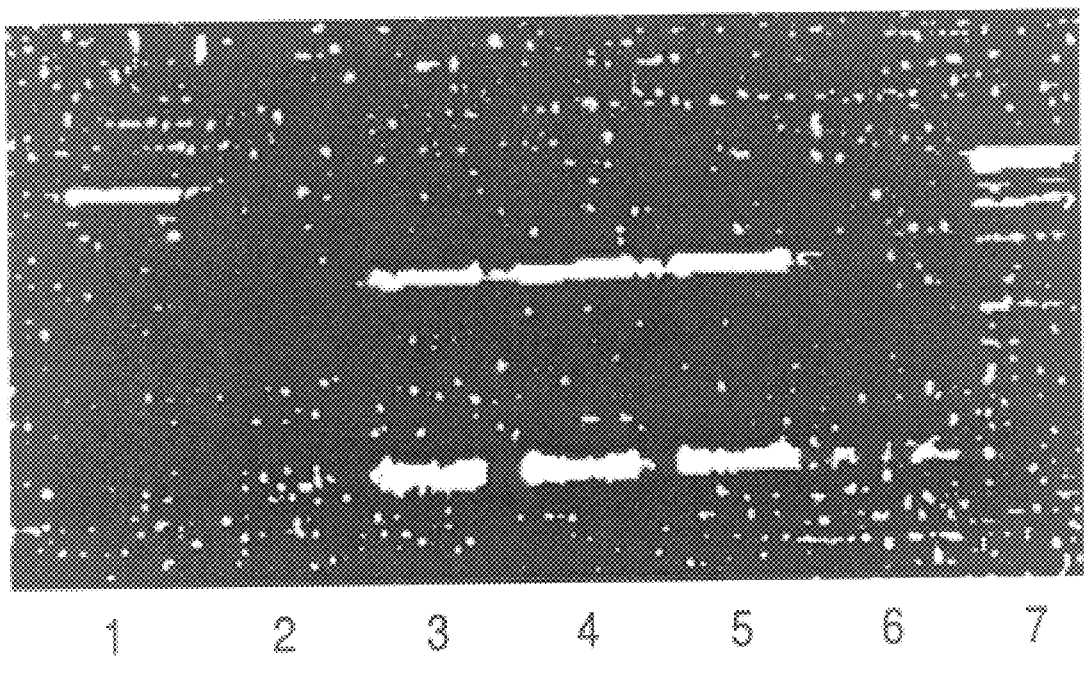

FIG. 6A. Effect of DTT (dithiothreitol) concentration in the translation reaction on generation of functional antibody in ARM display. Messenger RNA encoding DB3 VH/K was generated in an in vitro transcription reaction and added to the flexi Rabbit Reticulocyte Lysate system (Promega), which allows DTT to be added separately Track 1. 7: Marker, track 2: untranslated mRNA control, track 3: 0 DTT, track 4: 2 mM DTT. track 5: 5 mM DTT, track 6: 10 mM DTT. The result shows that 0, 2 mM and 5 mM DTT all produced good ARM recovery, while only at 10 mM was there an inhibition.

FIG. 7. Optimisation of Mg$^-$ concentration for ARM display.

FIG. 8. Optimisation of time course of ARM display.

FIG. 9. Efficiency of recovery of input mRNA, cDNA recovered from the ARM cycle (left hand four tracks) is compared with cDNA recovered directly from the mRNA (right hand tracks), in each case by RT-PCR.

Figure 10:
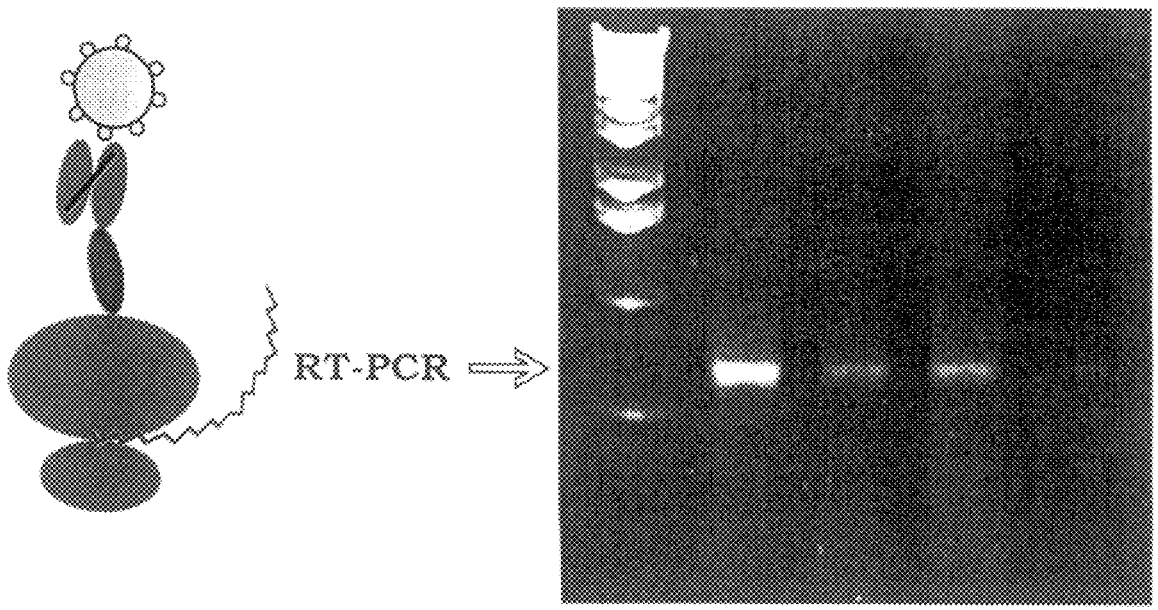

FIG. 10. Input sensitivity of ARM display, i.e. how little DNA can be used per cycle. In this experiment, the recovery primer combination was T7 and D4 (FIG. 2A). (Note that the original photograph shows a faint but clearly discernable band at 10 pg).

Figure 11:
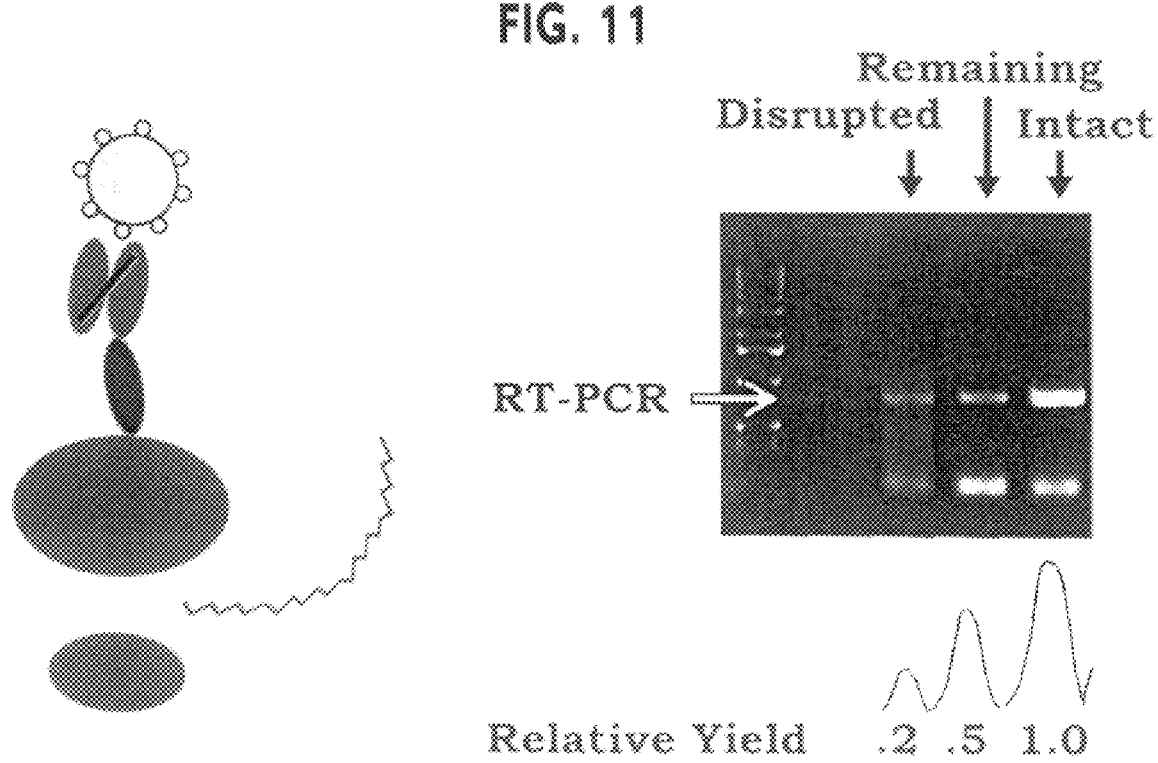

FIG. 11. Comparison of the method (according to the invention) of recovery of cDNA without ribosome disruption, with that of prior art technology which requires ribosome disruption. The track labelled 'Intact' shows the recovery of cDNA by the present invention, i.e. on the intact ribosome without disruption; 'Disrupted' refers to recovery of cDNA by the prior art method of ribosome disruption using 20 mM EDTA and subsequent isolation of mRNA before RT-PCR; and 'Remaining' is recovery of cDNA using the method of the present invention from mRNA remaining associated with the ribosome after disruption according to the prior art method. The relative yields from the 3 recovery reactions was determined by densitometry.

FIG. 12. (SEQ ID NOS 40–52) Error rate per cycle. The occurrence of errors during a single cycle of selection of DB3 VH/K ARM was determined by cloning the recovered product after RT-PCR and comparing the sequences of clones with that of the native DB3. Substitutions are highlighted in bold type.

FIG. 13. Enrichment of a specific antibody fragment from a library of mutants: analysis by cloning. $DB3^{H35}$ (nonprogesterone-binding) $V_H/K$ was engineered such that the unique HincII site was removed; after ARM selection, treatment with HincII produced a single band of ~800 bp. In contrast, similar digestion of $DB3^R$ produces 2 fragments of ~500 bp and 300 bp. This enables clones containing $DB3^R$ to be distinguished from $DB3^{H35}$ by HincII digestion and gel anaylsis, as shown. $DB3^R$ ARM complexes were selected from mixtures with $DB3^{H35}$ nonbinding mutants at ratios of 1:10 to 1:10$^5$. The resulting cDNA recovered after one cycle of selection was cloned; DNA was prepared from individual clones and analysed after HincII and EcoRI digestion. In each track, a doublet of bands at 500 and 300 bp indicates $DB3^R$ while a single band at ~800 bp is $DB3^{H35}$. 10 clones at each ratio were analysed after selection. The result demonstrates an enrichment factor of ~10$^4$ fold in one cycle. (See Example 10).

Figure 14:
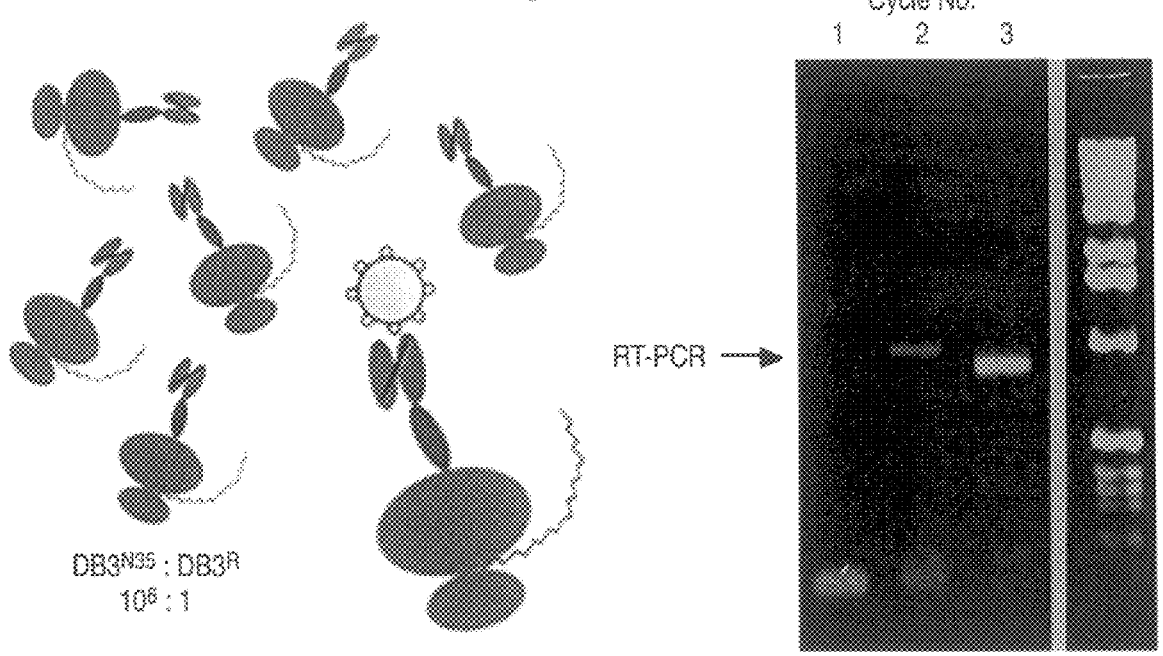

FIG. 14. Enrichment of $DB3^R$ from a 1:10$^6$ ratio library ($DB3^R$:$DB3^{H35}$) by repeated ARM display cycles. Selection was with progesterone-BSA coupled beads. Track 1, 1 kb DNA marker; 2, RT-PCR after first cycle; 3, RT-PCR after second cycle; 4, RT-PCR after third cycle. The shortenening of the band between cycles 2 and 3 is due to the use of different primers (D3, D4 respectively).

Figure 15:
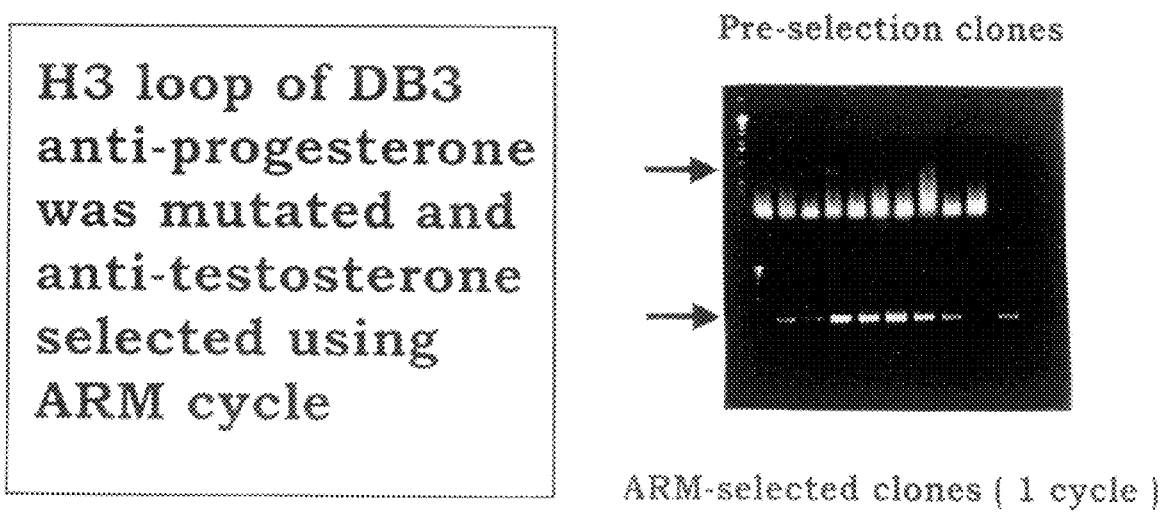

FIG. 15. Changing antibody specificity by mutagenesis and ARM selection (1). DB3 specificity was changed from progesterone-binding to testosterone-binding by mutagenesis of the H-CDR3 loop, followed by a single cycle of ARM selection. Specificity of individual clones was analysed by ARM display, selecting with testosterone-BSA coupled beads. Upper panel: pre-selection clones; lower panel: post-selection clones.

Figure 16:
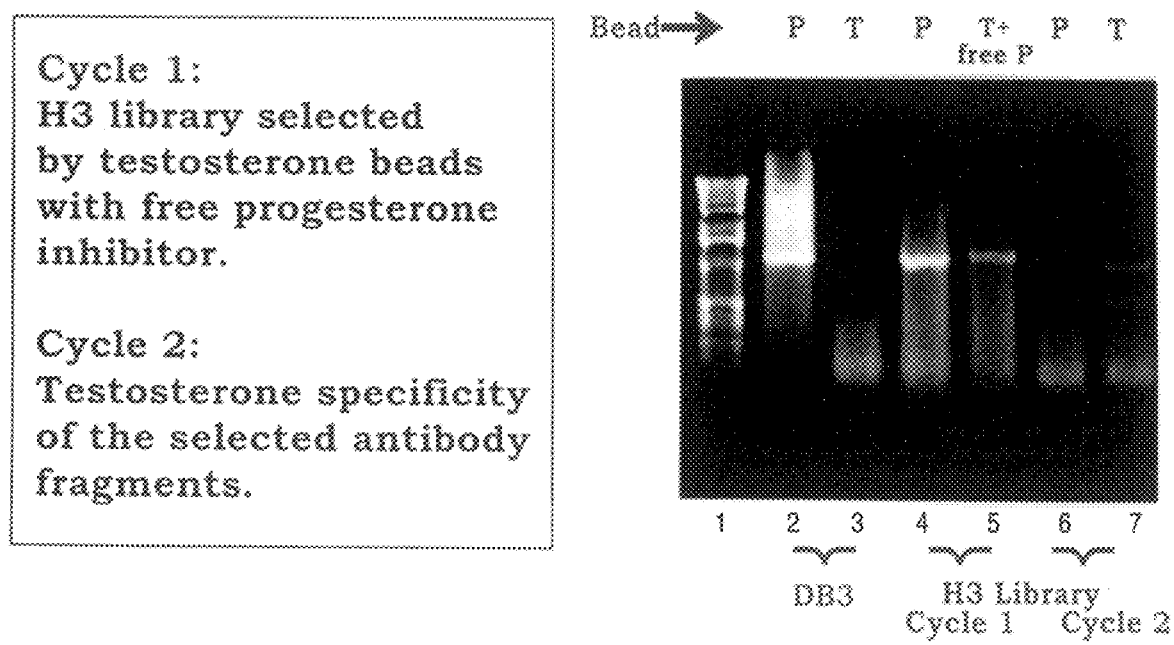

FIG. 16. Changing antibody specificity by mutagenesis and ARM selection (2): Selection of DB3 H3 mutants by testosterone-BSA beads in the presence of free progesterone as inhibitor. Track 1: marker; Tracks 2,3: binding of DB3$^R$ to progesterone-BSA (P) or testosterone-BSA (T) beads; Tracks 4,5: binding of the DB3 H3-mutant library to P beads, or to T beads in the presence of free progesterone; Tracks 6,7: the DNA product of track 5 was put into a further ARM display cycle and reselected on P or T beads. (Note the original gel photograph shows a distinct band in track 7).

Figure 17:
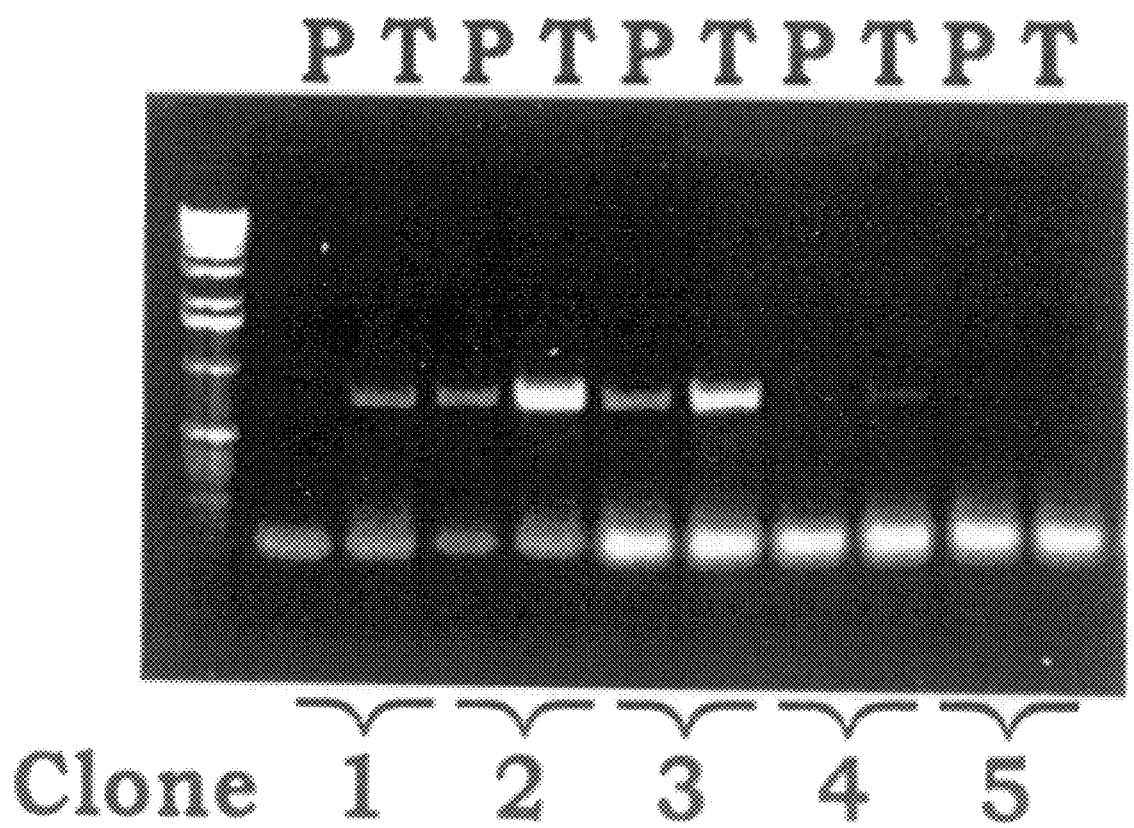

FIG. 17. Changing antibody specificity by mutagenesis and ARM selection (3). Steroid binding of 5 individual clones after selection by testosterone beads was analysed by ARM display and binding to progesterone-BSA beads (P) and testosterone-BSA beads (T).

Figure 18:
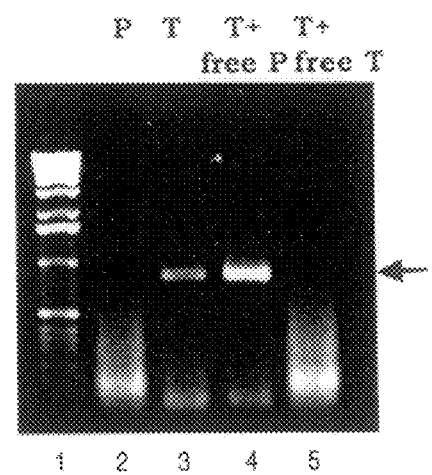

FIG. 18. (SEQ ID NOS 53–54) Changing antibody specificity by mutagenesis and ARM selection (4): Characterisation of a testosterone-specific clone derived by ARM display from the DB3 H3-mutant library. Tracks 1: marker; Tracks 2,3: binding of clone to progesterone-BSA (P) or testosterone-BSA beads (T); Tracks 4,5: binding of clone to T beads in the presence of free progesterone or free testosterone. The sequence of the H3 region of the mutated clone (mut) is shown.

FIG. 19. Sequences of human anti-progesterone and anti-testosterone antibodies isolated from an immunised transgenic mouse by ARM display.

Figure 20:
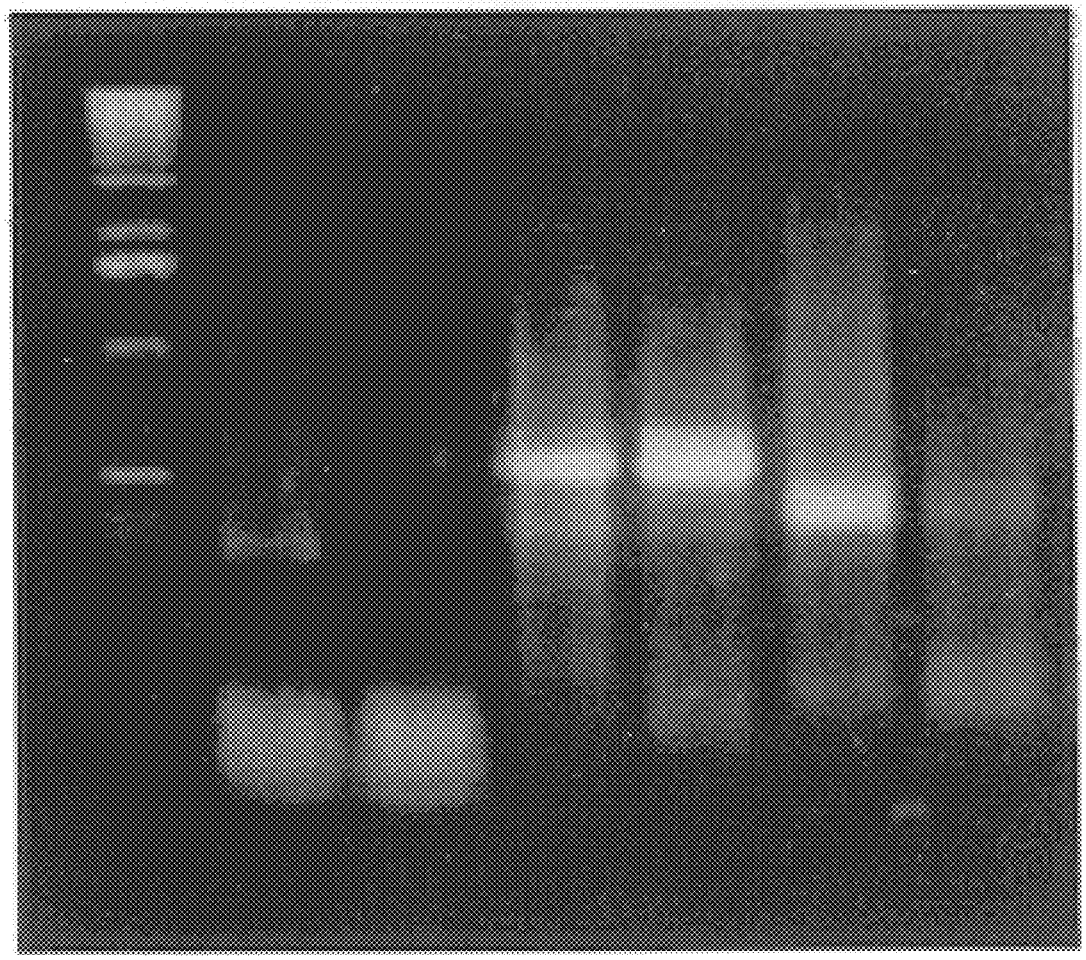

FIG. 20. Selection of genes from a total mRNA library from mouse spleen cells by ribosome display.

Track 1: Marker

Track 2: RT-PCR of λ light chain on total mRNA from mouse spleen cells.

Track 3: RT-PCR of λ light chain after in vitro translation of above mRNA and selection of ribosome complexes by anti-κ coated beads Track 4: RT-PCR of κ light chain on total mRNA from mouse spleen cells.

Track 5: RT-PCR of κ light chain after in vitro translation of the mRNA extract and selection of ribosome complexes by anti-κ coated beads.

Track 6: RT-PCR of Ig heavy chain from total mRNA from mouse B cells.

Track 7: RT-PCR of Ig heavy chain after in vitro translation of the mRNA extract and selection of ribosome complexes by anti-κ coated beads.

MATERIALS AND METHOD OF THE ARM RIBOSOME DISPLAY CYCLE (FIG. 1)

1. Single chain antibody constructs used to generate ARM complexes

The antibody combining sites used to test this method are in a form which we have previously described, namely three-domain single-chain fragments termed $V_H$/K, in which the heavy chain variable domain ($V_H$) is linked to the complete light chain (K) (10). We have described a DNA construct and bacterial expression system for producing an anti-progesterone antibody (DB3) as a $V_H$/K fragment (10) and both periplasmic and cytoplasmic expression were demonstrated (11). The DB3 $V_H$/K fragment has excellent antigen-binding properties, which in our hands are superior to those of the commonly used single-chain Fv (scFv) form. Using the 'megaprimer' PCR method (12) on plasmid DNA containing DB3 $V_H$/K, mutants at positions H100 and H35, binding site contact residues for progesterone (13), were produced (unpublished results). DB3$^R$ is a mutant in which tryptophan H100 was substituted by arginine, a modification which leads to an increased affinity for progesterone. DB3$^R$ expressed from *E. coli* bound strongly to progesterone (Ka ~$10^9$ M$^{-1}$) but had a much lower affinity for testosterone and none detectable for BSA. In contrast, a library of mutants generated at position H35 (designated DB3$^{H35}$) bound progesterone weakly or not at all. We have employed the DB3$^R$ and DB3$^{H35}$ mutants to test the principle of ARM selection.

2. Method for generation of ARM complexes

To generate $V_H$/K DNA fragments for production of ARMs, PCR was performed using appropriate templates together with (i) an upstream T7 primer, containing the T7 promoter, protein initiation sequence and degenerate sequence complementary to mouse antibody 5' sequences, and (ii) a downstream primer (D1), lacking a stop codon (FIG. 2A). The T7 primer sequence was [SEQ ID 3] 5'-gcgcgaatacgactcactatagagggacaaaccatgsaggtcmarctcgag sagtcwgg-3' (where s=c/g, m=a/c, r=a/g and w=a/t), and the D1 primer was [SEQ ID 4] 5'-tgcact ggatccaccacactcattcctgttgaagct-3', which contains a BamHI site (underlined) for cloning purposes. To prepare $V_H$/K constructs, standard PCR was carried out in solution containing 1×PCR reaction buffer (Boehringer Mannheim UK, Lewes, East Sussex), 0.2 mM dNTPs (Sigma), 0.3 μM of each primer, 0.05 U/μl of Taq polymerase (Boehringer Mannheim) with one or two drops of nuclease-free mineral oil overlayed on the top of the mixture. The following programme was used: 30 cycles consisting of 94° for 1 min, 54° for 1 min, 72°, for 1 min, then 72° for 10 min followed by 4°.

$V_H$/K PCR constructs (1 ng–1 μg) either purified by QIAquick (QIAGEN) or unpurified, were added to 20 μl of the TNT T7 quick coupled transcription/ translation system (Promega UK Ltd, Southampton, Hants SO16 7NS, UK) containing 0.02 mM methionine and the mixture incubated at 30 for 60 min. The protocol can be scaled down to 10 μl. After translation the mixture was diluted with an equal volume of cold phosphate-buffered saline and cooled on ice for 2 min. (For optimisation of conditions, see the description in Examples 4 and 5 below).

3. Modification of the primers

The upstream T7 primer, including the T7 promoter and protein initiation signal, can be modified with improved yield. The modified sequence is [SEQ ID 5] 5'-gcagctaatacgactcactataggaacagaccaccatgsaggtcrcarctcg agsagtcwgg, as shown in FIG. 2B.

4. Antigen selection of ARM complexes

Magnetic beads (Dynal, UK) were coupled to bovine serum albumin [BSA], progesterone-11α-BSA, testosterone-3-BSA (Sigma-Aldrich Co. Ltd., Poole, Dorset, UK) or purified rat anti-mouse κ antibody (gift of Dr G Butcher) according to manufacturer's instructions. 2–3 μl of antigen- or anti-κ-conjugated magnetic beads were added to the translation mixture and transferred to 4° for a further 60 min, with gentle vibration to prevent settling. The beads were recovered by magnetic particle concentrator (Dynal MPC), washed 3 times with 50 μl cold, sterilised phosphate buffered saline (PBS), pH7.4, containing 0.1% BSA and 5 mM magnesium acetate, and once with PBS alone. In order to remove possible DNA contamination, the beads were treated at 37° C. for 25 min with DNase I (Promega or Boehringer Mannheim) in 50 μl Dnase I buffer (40 mM Tris-HCl, pH7.5, 6 mM $MgCl_2$, 10 mM NaCl, 10 mM $CaCl_2$) containing 10 units of enzyme, followed by three washes with 50 μl PBS containing 1% tween-20, 5 mM magnesium acetate and resuspension in 10 μl of diethylpyrocarbonate-treated water.

5. Recovery and amplification of genetic information from antigen-selected ARM complexes.

To produce and amplify cDNA from the mRNA of antigen-selected ARMs, RT-PCR was performed by adding 2 μl of the above bead suspension to 23 μl of the RT-PCR mixture (Titan One-tube RT-PCR System, Boehringer Mannheim, or Access RT-PCR system, Promega UK Ltd) containing 1 μM of each primer. The primers were the upstream T7 primer described above and a new downstream primer, D2, sequence 5'-cgtgagggtgctgctcatg-3', designed to hybridise at least 60 nt upstream of the 3'-end of ribosome-bound mRNA (FIG. 2A). The use of this primer avoids the need to isolate the mRNA from ARM complexes (FIG. 1). The reaction mixture was overlayed with one or two drops of nuclease-free mineral oil and placed in a thermal cycler (Techne Progene). The program for single-step RT-PCR was: one cycle at 48° for 45 min, followed by one at 94° for 2 min, then 30–40 cycles consisting of 94° for 30 sec, 54° for 1 min, and 68° for 2 min; finally one cycle at 68° for 7 min was followed by 4°. PCR products were analysed by agarose gel electrophoresis and eluted from the gel for sequencing.

6. Further cycles of ARM complex generation and selection, and primer combinations for efficient recovery in sequential cycles For further cycles, the PCR products produced as above were either gel-purified or added directly to the TNT transcription/translation system. In a second cycle, the RT-PCR downstream primer D3, sequence [SEQ ID 11] 5'-ggggtagaagttgttcaagaag-3', was designed to hybridise upstream of D2 (FIG. 2A); similarly in the third cycle the primer D4, [SEQ ID 12] 5'-ctggatggtgggaagatgg-3', hybridising upstream of D3, was used (FIG. 2A). The recovered DNA becomes progressively shorter in each cycle, but a full length $V_H$/K can be regenerated in any cycle by recombinational PCR. Moreover, the shortening only affects the constant domain of the light chain, not the antigen-binding region.

In this protocol, each cycle required a new downstream primer (D2, D3, D4) due to the fact that the 3' end of the mRNA is covered by the ribosome and inaccessible to primer. While this avoids the need to separate the mRNA from the ribosome, it also causes as noted a shortening of the recovered cDNA in each cycle. We have now overcome this problem by designing a new primer called EVOU, which incorporates D2 and extends downstream restoring most of the 3' cDNA sequence and which can be used in every cycle.

As is shown in FIG. 2B, the sequence of the EVOU primer, is: 5'-gctctagaggcctcacaggtatagctgttatgtcgttcatactcgtccttggt-caacgtg agggtgctgctcat-3' [SEQ ID 13] bold=XbaI site Experiment shows that recovery of cDNA occurs when a mixture of D2 and EVOU are used together in the recovery RT-PCR (Example 1, FIG. 4). The unexpected feature of the result is that use of the primer mixture gives just one band of the expected full length whereas two bands were expected. This is probably explained by the efficiency of the EVOU primer under the PCR conditions used, leading to a clean and ideal result.

Therefore, in the preferred method, the primers are the upstream T7 primer and the downstream primer D2, sequence [SEQ ID 14] 5'-cgtgagggtgctgctcatg-3', designed to hybridise at least 60 nt upstream of the 3' end of ribosome-bound mRNA, plus the primer EVOU which incorporates D2, as in FIG. 2B.

For further cycles, the PCR products produced as above were either gel-purified or added directly to the TNT transcription/translation system. The combination of D2 and EVOU primers was used in the RT-PCR at the each subsequent cycle. The recovered DNA is thus the same length in each cycle. (FIG. 4).

7. Primers for human VH/K antibody fragments

The above primers and those shown in FIG. 2 are applicable for VH/K fragments from all mouse immunoglobulins. For human antibodies the corresponding primers are:

T7 primer: 5'-gcagctaatacgactcactataggaacagaccaccatgsaggtmcasctc-gagsagtctgg [SEQ ID 6], and D1 primer: gctctagaacactttcccctgttgaagct [SEQ ID 7]
D2 primer: gctctagagctcagcgtcagggtgctgct [SEQ ID 8]
D4 primer: gctctaeagaagacagatggtgcagc [SEQ ID 9]
EVOU primer: cgaattctctaatgatggtgatggt-gatggtagactttgtgtttctcgtagtctgcttt gctcagcgtcagggtgctgct [SEQ ID 10]

(enzyme sites are underlined; hexahistidine tag is in italics).

RESULTS

EXAMPLE 1

Recovery of DNA by RT-PCR on the Ribosome Complex and Use of 2- or 3-Primer Combinations In the ARM method (FIG. 1), the ribosome is stalled and the stable complex (nascent protein-ribosome-mRNA) forms because of the absence of a stop codon at the 3' end of the message. Since the ribosome is stalled at the 3' end of the mRNA, the latter should be inaccessible to a 3' primer and/or to reverse transcriptase, necessitating the use of an upstream primer in the recovery of cDNA. This is confirmed by the experiment in FIG. 3. When full length DB3 DNA, lacking the 3' stop codon, was transcribed and the mRNA translated in vitro and selected with progesterone-BSA beads, cDNA recovery showed that the 3' end of the mRNA was not available for priming in RT-PCR, whereas an upstream primer (D2, FIG. 2A) successfully recovered the cDNA. Likewise, in a second cycle, D2 was no longer effective and a primer further upstream (D3, FIG. 2A) was required. Thus, the concept of a ribosome bound to the 3' end of the mRNA in the ARM complex appears to be correct. This experiment demonstrates the recovery of cDNA by RT-PCR on the ribosome-mRNA complex.

Clearly, the repeated use of the ARM cycle in this way leads to shortening of the recovered cDNA and eventually it would become necessary to restore full length by a recombinational PCR reaction. However, in the modified procedure, the use of the D2 primer in combination with the EVOU primer (FIG. 2B) restores the full length in every cycle. FIG. 4 shows the recovery of the full length VH/K cDNA over 5 cycles. The ARM cycle was performed as described and the combination of primer D2 (labelled as RT primer) and EVOU (PCR primer) was used for recovery. The recovered product DNA was then applied in 4 further sequential cycles in the same way and the products analysed in each case. As shown the full length of VH/K of about 1 kb is recovered in each cycle and the DNA was confirmed by sequencing.

The use of these primer combinations leads to efficient recovery of cDNA without the need to isolate the mRNA separately by dissociation of the polysome, as described by others. It is a quick and efficient way of recovering the genetic information as DNA (see also Example 8).

EXAMPLE 2

Antigen-Specific ARM Selection

To demonstrate antigen-specific ARM selection, $DB3^R$ $V_H/K$ was translated in vitro and ARMs exposed to magnetic beads coupled either to progesterone-11α-BSA, testosterone-3-BSA or BSA alone. After RT-PCR, a single DNA fragment was detected only from progesterone-11α-BSA coupled beads (FIG. 5A, tracks 2,4,6), consistent with the known specificity of $DB3^R$ $V_H/K$. The recovered fragment was further confirmed as $DB3^R$ by sequencing. No bands were obtained when PCR alone, rather than RT-PCR, was carried out on the progesterone-11α-BSA beads after selection (FIG. 5A, tracks 3,5,7), or when the procedure was performed with nontranslated $DB3^R$ mRNA (FIG. 5A, track 1). Thus, the band recovered by RT-PCR is derived from mRNA selected via the functional antibody combining site of $DB3^R$ and not from DNA contamination or mRNA carryover.

EXAMPLE 3

Inhibition by Free Antigen of ARM Binding to Immobilised Antigen Demonstrates Correct Folding of the VH/K on the Ribosome Inhibition by free steroids can be used to demonstrate the correct folding and functional activity of the ARM complex (FIG. 6). The inhibition of DB3 $V_H/K$ expressed as an ARM, using different steroidal inhibitors, is indistinguishable from that of native DB3 and recombinant $V_H/K$. Furthermore, the 50% inhibition by progesterone-11α-HMS at 1 ng (2.5 nM) indicates an affinity very close to that of DB3 (data not shown).

The free steroid inibitors were added to the DB3 ARM mixture in order to block binding to the progesterone-coated beads. They are progesterone-11α-hemisuccinate (HMS) (P11), progesterone-3-carboxymethyloxime (P3); progesterone-6-HMS (P6) and progesterone-21-HMS (P21). The inhibition of free DB3 $V_H/K$ in an ELISA reaction is shown on the right, with the efficiency of the steroids in the order P11>P3>P6>P21. A very similar order of reaction and concentration is seen for the nascent DB3 $V_H/K$ on the ribosome as an ARM (the central panel shows representative results of the recovery RT-PCR reaction).

This demonstration of fine specificity confirms that the nascent antibody $V_H/K$ fragment is correctly folded in the ARM complex. Similarly, there is no requirement for addition of chaperones in the rabbit reticulocyte system, whereas this is also desirable in the prokaryotic system (15). It is possible that the eukaryotic ribosome itself plays a contributory role in folding of the nascent polypeptide chain (25).

EXAMPLE 3A

Optimal DTT Concentrations for ARM Display

It has been contended that single chain antibodies may not fold correctly in the presence of 2 mM dithiothreitol (DTT), which is present in the transcription/translation reaction mixture, but this appears not to be the case, as shown in FIG. 6A. The ARM cycle was carried cut in the presence of various concentrations of DTT from 0–10 mM by translating DB3 VH/K mRNA, produced in a separate transcription in vitro; the translation reaction was performed in the flexi Rabbit Reticulocyte Lysate system (Promega), which allows DTT to be added. The result in FIG. 6A shows that 0, 2 mM and 5 mM DTT all produced good ARM recovery (Tracks 3–5), while only at 10 mM was there an inhibition (Track 6). Hence, 2 mM DTT does not adversely effect folding and recovery. Thus, protein disulphide isomerase PDI, which is stated as being important for folding of antibody domains in the prokaryotic E. coli S30 system (15), is not required for eukaryotic ribosome display in the rabbit reticulocyte system.

EXAMPLE 4

Optimisation of Magnesium Concentration (FIG. 7)

Magnesium acetate in varying concentrations was added to the TNT transcription/translation reaction system and the recovery of DNA after the ARM cycle was compared. Optimal yield was acheived at 0.5 mM Mg acetate.

EXAMPLE 5

Optimisation of Time Course (FIG. 8)

In the ARM cycle, coupled transcription/translation was carried out for various times in order to determine the optimal time-course of the reaction. This is shown to be 60 minutes incubation, after which time there was no improvement in recovery.

EXAMPLE 6

Efficiency of Recovery of Input mRNA (FIG. 9)

In order to assess the efficiency of recovery of mRNA during a single ARM cycle, mRNA for DB3 VH/K was prepared separately by transcription in vitro. The cDNA recovered after the processes of translation, ARM complex selection on progesterone beads and RT-PCR on the complexes was compared with that recovered directly from the unmanipulated input mRNA. The left hand 4 tracks show a titration of the cDNA obtained after recovery from the ARM cycle, while the right hand 4 tracks show that obtained from the input mRNA. Densitometry shows that about 60% of the possible cDNA is actually recovered after ARM selection. To produce this result, 60% of the mRNA must be translated into fully functional antigen-binding protein. This recovery yield should be compared with 2% reported by Mattheakis et al. (14) and 0.2% by Hanes and Pluckthun (15) and demonstrates the greatly increased efficiency of the present method.

EXAMPLE 7

Sensitivity of the ARM Cycle for Input DNA (FIG. 10)

An essential parameter in the efficiency of the system is the sensitivity for input DNA, i.e. how little DNA can be used per cycle. This experiment, in which DNA input was titrated, shows that a band can be recovered with an input as low as 10 pg. The running amount used routinely is 1–10 ng (tracks 2 and 3). The sensitivity of the prokaryotic methods by titration is not reported, but the amount used in the Mattheakis method (14) is 440 ng and by Hanes and Pluckthun (15) is 10 μgm. It is quite likely that the additional steps employed by the latter, namely recovery of mRNA prior to translation and again prior to reverse transcription, add greatly to the DNA requirement. This can be a critical element in the use of the method to search large libraries. For example, with an input of 1 pgm DNA, and a sensitivity of 10 pgm, it should be possible to obtain an enrichment of $10^5$ fold in a single cycle, which is what we have found (see Example 10). With lower DNA sensitivity, as appears to be the case in the prokaryotic systems, either considerably more DNA would have to be put in, or more selection and recovery cycles carried out.

EXAMPLE 8

Comparison of the Method (According to the Invention) of Recovery of cDNA without Ribosome Disruption with that of Prior Art Technology which Requires Ribosome Disruption (FIG. 11)

In order to determine the extent to which our procedure for recovery of cDNA at the end of the display cycle, i.e. by RT-PCR on the intact complex, is more efficient than the prior art of Kawasaki (16), Mattheakis (14) and Hanes and Pluckthun (15), we have duplicated their methods by disruption of the ribosome complex and recovery of RNA before RT-PCR. The disruption method followed that described by Hanes and Pluckthun (15): elution buffer was 50 mM Tris/acetate pH7.5, 150 mM NaCl, 20 mM EDTA; 100 μl was added to beads and incubated at 4° C. for 10 min; released RNA was recovered by precipitation with ethanol (standard procedure).

In the gel (FIG. 11), the track labelled Intact shows our recovery after one cycle; the track labelled Disrupted is recovery by the disruption method; and track labelled Remaining is what is left behind on the ribosome after disruption. The relative yields were compared by densitometry and showed that recovery performed with the mRNA attached to the ribosome is 5× more efficient than ribosome disruption when applied to the eukaryotic system, and that with the disruption procedure a considerable proportion of the mRNA remains attached to the ribosome and is thus effectively lost. Thus the recovery of cDNA by RT-PCR on the ribosome complex is an important contribution to the increased efficiency of the invention over prior art.

EXAMPLE 9

Accuracy Per Cycle (FIG. 12)

An important aspect of the invention is its capacity for gradually modifying proteins in vitro, taking advantage of the introduction of random point mutations by the several polymerase reactions included in the cycle followed by ligand-based selection, i.e. protein evolution. At the same time, a very high rate of mutation might render the system nonfunctional by damaging protein structure or combining site specificity. We therefore assessed the errors which are introduced per cycle by cloning the products of an ARM cycle in which DB3 was selected by progesterone-BSA beads. The result in FIG. 12 shows an error rate of 0.54%, which is low enough to maintain structure but high enough steadily to introduce useful mutations to evolve improved protein capabilities, such as antibody binding site affinity.

EXAMPLE 10

Selection of an Individual Antibody Combining Site from ARM Display Libraries in a Single Cycle. (FIGS. 5 and 13).

Another important application of ribosome display is the selection of antibodies, or other proteins, from libraries of mutants. To investigate such selection and determine the enrichment possible by eukaryotic ribosome display, $DB3^R$ was mixed with random $DB3^{H35}$ mutants which bind progesterone weakly or not at all (in the mutants, the H35 codon AAC was mutated to C/G T/A/G A). When the $DB3^{H35}$ mutant library alone was displayed as ARM complexes, no DNA band was recoverable after selection with progesterone-11α-BSA beads (FIG. 5B, track 3; FIG. 5C, track 6); translation of DB3 H35 was demonstrated by the band obtained with beads coated with rat anti-κ antibody (FIG. 5B, track 4). When DNA mixtures containing $DB3^R$ and $DB3^{H35}$ mutants in ratios ranging from 1:10 to $1:10^5$ were displayed as ARMs, a band of $V_H/K$ size was in all cases recovered after a single cycle (FIG. 5C, tracks 1–5). Selected DNA was sequenced and, based on codon detection, it was shown that whereas before selection $DB3^R$ was not detectable in the $1:10^3$–$1:10^5$ libraries, it was the predominant molecule selected from the $1:10^3$ ratio library and a major component of the PCR product from the $1:10^4$ and $1:10^5$ ratio libraries. Thus, enrichment in the range of $10^4$–$10^5$ fold is achievable in a single cycle of ARM selection.

Because sequencing of a mixed PCR product may not be sufficiently sensitive to provide accurate information on enrichment, in particular to define the ratio of selected:non-selected (background) species, a further means of discriminating between $DB3^R$ and $DB3^{H35}$ mutations was introduced. A unique HincII enzyme site was removed from $DB3^{H35}$ but left in $DB3^R$. Thus, HincII digestion caused a reduction in size of the $V_H/K$ for $DB3^R$ from 800 bp to two fragments of 500 bp and 300 bp, whereas $DB3^{H35}$ mutants were not cleaved and ran as a fragment of ~800 bp. After selection from mixtures in the same ratios as above, the RT-PCR products were cloned and DNA from individual clones mapped by digestion with EcoRI and HincII enabling quantitation of the proportion of $DB3^R$ and $DB3^{H35}$ clones recovered. As shown in FIG. 13, 70% of the clones selected from a $1:10^4$ library and 40% from a $1:10^5$ library were $DB3^R$. This gives calculated enrichment factors of ~$10^4$ fold, which is in agreement with the previous data from direct sequencing of PCR mixtures (above). It is possible that even greater enrichment could be obtained by use of larger amount of DNA in the cycle. These enrichment values are considerably higher than those reported for prokaryotic systems of 100-fold (15) or 40-fold (23).

EXAMPLE 11

Selection of an Individual Antibody Combining Site from an ARM Display Library in Two or Three Cycles (FIG. 14)

While a $1:10^6$ $DB3^R:DB3^{H35}$ library did not produce a detectable RT-PCR band after one cycle (FIG. 14, track 2), two further cycles of ARM generation and selection led to recovery of a $V_H/K$ band, with increased intensity at each repetition (FIG. 14, tracks 3,4). Sequencing again confirmed the selection of $DB3^R$.

EXAMPLE 12

Changing Antibody Specificity by Mutagenesis and ARM Selection from a Mutant Library (Antibody Engineering) (FIGS. 15–18)

The affinity of the DB3 antibody for progesterone is 7,000 times greater than that for testosterone. We attempted to reverse this specificity by combining mutagenesis of the H3 loop (CDR3 of the heavy chain) with ARM display. An H3 mutant library, consisting of 3×10$^7$ members without stopcodons, was produced by random mutagenesis of DB3$^R$ residues 98, 99, 101, 102 and 103. Individual clones from this library, before ARM selection, were analysed by in vitro expression in the ARM format as described. In FIG. 15, the upper part of the gel (pre-selection clones) shows that there was little or no recovery of cDNA after binding to testosterone-3-BSA-coupled beads. The mutant library was then displayed as ARM complexes and selected in one cycle by binding to testosterone-3-BSA beads. The recovered cDNA was cloned; individual clones now mostly showed positive binding to testosterone-BSA with strong recovery reflecting good binding (lower part of the gel). This demonstrates that the ARM display method is effective in selective enrichment of mutant clones with new antigen-binding properties and that the ARM system can be used for rapid analysis of binding activity of antibody clones.

The library was then selected against progesterone-BSA and testosterone-BSA beads. For the latter, free progrestereone-11α-hemisuccinate was present to block all progesterone binding, hence the effect should be to switch specificity completely to testosterone if such binders are present in the library. In FIG. 16, the centre tow tracks show this result and demonstrate that the library contains mutants capable of binding specifically to testosterone. The cDNA recovered after binding to testosterone-BSA beads in the presence of free progesterone was recycled against progesterone and testosterone beads and showed specificity for testosterone (tracks 6, 7). This result implies that specificity could be switched from binding of one ligand to another. (Note, the band in track 7 is clearly visible on the original photograph).

To confirm the specificity of the cDNA recovered in track 6 of FIG. 16, its specificity was also examined by cloning. FIG. 17 shows the analysis of individual clones expressed as ARM complexes in vitro and tested for binding to progesterone-BSA and testosteron-BSA beads. Out of 5 clones analysed, 3 bound preferentially to testosterone, demonstrating the conversion in specificity from solely progesterone-binding (DB3$^R$) to preferential binding of testosterone (clones 1–3).

One of the clones obtained through mutagenesis and selection against testosterone in the presence of free progesterone was analysed by ARM display and DNA sequencing. In FIG. 18, it is seen that the mutant testosterone-binding clone bound specifically to beads coupled to testosterone-3-BSA (T) with no cross-reaction with progesterone-11-BSA (P), and that it could be specifically inhibited by free testosterone-3-BSA (T) but not by free progesterone (P).

These results demonstrate that the ability of ARM display to select from large libraries can be used in conjunction with mutagenesis to carry out antibody engineering, in particular to bring about the alteration of antibody specificity through steps of mutation and selection.

EXAMPLE 13

Selection of Human Antibodies from Libraries Prepared from Transgenic Mice. (FIG. 19)

An area of great interest is the use of display methods to isolate human antibodies which can be used for in vivo diagnostic or therapy in man. The source of such a library can be human lymphocytes from naturally immune or actively immunised individuals. However, in order to respond to human antigens, many of which are important therapeutic targets, the human lymphocytes must develop in a nontolerising environment. This can be achieved through the use of transgenic mice, which have acquired the genes encoding human heavy and light chains in their genomes through embryo manipulation; the ability of these mice to make endogenous mouse antibody has been eliminated by introduction of knock-out deletions (20). Such mice respond to immunisation with human antigens by production of human antibodies (20). We have immunised mice carrying a human heavy chain translocus comprising 5 $V_H$ genes, the complete D-J region and the Cμ and Cδ genes, together with a light chain translocus carrying 8 $V_L$ genes, the entire J region and the Cκ gene. The mice were immunised with progesterone-11α-HMS-BSA and after 8 weeks the spleens were removed. A $V_H$/K DNA library was prepared by RT-PCR amplification of the expressed $V_H$ and light chain genes followed by random combination through the standard $V_H$/K linker sequence, using recombinational PCR; the stop codon was deleted from the 3' end of the light chain. The library was expressed in vitro as ARM complexes and selected using progesterone-BSA or testosterone-BSA coupled magnetic beads. Recovered cDNA was cloned and sequenced (FIG. 19). The sequences enabled human VH and VL genes to be identified and the CDR3 regions of the heavy chain to be compared. While there is repetitive selection of two human VH/VL combinations (VH4/Vk1-12 and VH1-2/Vk4-01) there is considerable diversity in the H3 sequences. However, one of the steroid contact residues identified from crystallography in the VH CDR2 of anti-steroid antibodies (W50, the first CDR2 residue) is universally present and a relevant aromatic is also present around residue 100.

EXAMPLE 14

Selection of Genes from an mRNA Library by Eukaryotic Ribosome Display, FIG. 20

Although the examples cited thus far have all related to expression and selection of antibody fragments, ribosome display should be applicable to any protein which retains a selectable functionality, such as a binding site or an epitope, when bound in nascent form on the ribosome. Thus, it should be possible to isolate genes from cDNA or mRNA libraries in the ribosome display format, e.g. selecting complexes with antibody- or ligand-coupled particles.

This example demonstrates the use of ribosome display (1) to select a gene encoding an expressed protein starting with an mRNA extract obtained from mammalian cells, (2) to select a specific mRNA as a ribosome complex using an antibody attached to beads as the selecting agent, and (3) to recover the relevant gene by RT-PCR carried out on the ribosome-bound mRNA. For the library, mRNA was extracted by Pharmacia mRNA purification kit and directly expressed in vitro using the Promega TNT transcription/translation system. No attempt was made to remove the stop codon, but instead the reaction was stopped after 1 hour by cooling on ice. The translation mixture was exposed to monoclonal rat anti-κ antibody linked to magnetic beads. Bound mRNA was converted to cDNA and amplified by RT-PCR using specific primers for the κ chain and, as negative controls, for λ light chain and IgG heavy chain. The results are shown in FIG. 20. The cDNA bands in tracks 2, 4 and 6 were obtained directly from the mRNA library and show that mRNA for human λ and κ light chains and heavy chain respectively were present. After the expression of the mRNA in ribosome display format and selection with anti-κ coated beads, a strong κ light chain band was recovered after RT-PCR (track 4), with no band for λ light chain (track 3) and a weak band for heavy chain (track 7), thus demonstrating the specific selection and recovery of κ chain cDNA. To our knowledge, this is the first experiment to show the selection of a protein from a natural library (i.e. derived from a normal tissue) by ribosome display.

CONCLUSIONS

The greater efficiency of this display method over those previously described can be seen as deriving from a number of factors, the use of a eukaryotic expression system, coupled transcription and translation, stalling the ribosome by eliminating the stop codon and efficient recovery by RT-PCR carried out on the ribosome complex. Thus no time or material is consumed in isolating mRNA at different stages (after transcription, after selection) as in the Hanes and Pluckthun description. The novel step is the one of recovery, which we have demonstrated to be superior to ribosome dissociation. It is also likely to be much more economical due to the fact it allows much smaller amounts of mRNA to be handled in the system, which is clearly important when selecting rare molecular species from large libraries. We have shown that very small amounts of input DNA can be recovered, making it practicable to use large libraries.

REFERENCES (1) Smith, G. P. (1985) *Science* 228 1315–1317.
(2) Georgiou, G., Poerschke, H. L., Stathopoulos, C. and Francisco, J. A. (1993) *TIBTECH* 11 6–10.
(3) Kasahara, N., Dozy, A. M. and Kan, Y. W. (1994) *Science* 266, 1373–1376.
(4) Winter, G., Griffiths, A. D., Hawkins, R. E. and Hoogenboom, H. R. (1994) *Annu. Rev. Immunol.* 12, 433–455.
(5) Wrighton, N. C., Farrell, F. X., Chang, R., Kashyap, A. K., Barone, F. P., Muleshy, L. S., Johnson, D. L., Barrett, R. W., Jolliffe, L. K. and Dower, W. J. (1996) *Science*, 273, 458–463.
(6) Kretzschmar, T., Zimmermann, C. and Geiser, M. (1995) *Anal. Biochem.* 224, 413–419.
(7) Nicholls, P. J., Johnson, V. G., Andrew, S. M., Hoogenboom, H. R., Raus, J. C. M. and Youle, R. J. (1993) *J. Biol. Chem.* 268, 5302–5308.
(8) High, S., Gorlich, D., Wiedmann, M., Rapoport, T. A. and Dobberstein, B. (1991) *J. Cell. Biol.* 113, 35–44.
(9) Fedorov. A. N. & Baldwin, T. O. (1995) *Proc. Natl. Acad. Sci.* 92, 1227–1231.
(10) He, M. Kang, A. S., Hamon, M., Humphreys, A. S., Gani, M. and Taussig, M. J. (1995) *Immunology* 84, 662–668.
(11) He, M. Hamon, M. Lui, H., Kang, A. S. and Taussig, M. J. (1995) *Nucleic Acids Res.* 23, 4009–4010.
(12) Sarkar, G. and Sommer, S. S. (1990) *Biotechniques* 8, 404–407.
(13) Arevalo, J., Stura, E. A., Taussig, M. J. and Wilson, L. A. (1993) *J. Mol. Biol.* 231, 103–118.
(14) Maltheakis, L. C., Bhatt, R. R. and Dower, W. J. (1994) *Proc. Natl. Acad. Sci. USA* 91, 9022–9026.
(15) Hanes, J. and Pluckthun, A. (1997) *Proc. Natl. Acad. Sci. USA* 94, 4937–4942.
(16) Kawasaki, G. U.S. Pat. Nos. 5,643,768 Cell free synthesis and isolation of novel genes and polypeptides (Jul. 1, 1997) and 5,658,754 (Aug. 19, 1997).
(17) Vaughan et al. (1996) *Nature Biotech.* 14, 309–314.
(18) PCT publication WO 95/1192, 'In vitro peptide and antibody display libraries', dated Oct. 25, 1994.
(19) Stansfield I., Jones K. M. and Tuite M. F. (1995) *Trends in Biochem. Sci.* 20, 489–491.
(20) Bruggemann M. and Neuberger M. S. (1996) *Immunology Today* 17, 391–397.
(21) Marks J. D. et al. (1992) *BiolTechnology* 10, 779–783
(22) Hawkins R. E. et al. (1992) *J. Mol. Biol.* 226, 889–896.
(23) Roberts R. W. and Szostak J. W. (1997) *Proc. Nat. Acad. Sci USA* 94, 12297–12302.
(24) Laski F. A. et al. (1984) *EMBO Journal* 3, 2445–2452.
(25) Netzer W. J. and Hartl. F. U. (1998) *Trends in Biochem. Sci.* 23, 68–73.

This application claims priority to GB9710829.4, filed May 28, 1997, GB9724850.4, filed Nov. 26, 1997, and GB9804195.7, filed Feb. 28, 1998, the entirety of which is hereby incorporated by reference.

What is claimed is:

1. A method capable of (I) displaying and selecting proteins and peptides and (II) recovering genetic material selected from the group consisting of DNA and mRNA that encodes the proteins or peptides, wherein the method comprises:
   (a) transcribing DNA and translating mRNA therefrom in a eukaryotic cell free system in order to form complexed particles, wherein a complexed particle comprises at least one individual nascent protein or peptide associated with (i) one or more ribosomes and (ii) the mRNA encoding the protein or peptide;
   (b) contacting the complexed particles with a ligand, antigen or antibody;
   (c) selecting complexed particles using binding of the ligand, antigen or antibody to the protein or peptide of the complexed particle; and
   (d) conducting reverse transcription and polymerase chain reaction (RT-PCR) on the mRNA bound in the selected complexed particle from step (c) in order produce DNA encoding the protein or peptide.

2. A method according to claim 1, wherein the transcribing and translating are eukaryotic-based.

3. A method according to claim 1, wherein the transcribing and translating are coupled.

4. A method according to claim 1, wherein the transcribing and translating is performed with a rabbit reticulocyte lysate system.

5. A method according to claim 1, wherein the DNA and mRNA lack a stop condon.

6. A method according to claim 1, wherein the ligand, antigen, and antibody of step (b) is immoblized on insoluble supports.

7. A method according to claim 1, wherein the protein is a single chain antibody fragment.

8. A method according to claim 7, wherein the single chain antibody fragment comprises the variable region of the heavy chain ($V_H$) linked to the variable region of the light chain ($V_L$) (scFv fragment) or the entire light chain (K) ($V_H$/K fragment).

9. A method according to claim 1, further comprising (e) incorporating the RT-PCR product DNA into an expression vector, and (f) transforming a bacterium with the vector of step (e).

10. A method according to claim 1, wherein repeated cycles of ribosome display and selection are performed before recovering genetic information.

11. The method according to claim 1, wherein each complexed particle contains only one ribosome.

12. A method according to claim 1, wherein the complexed particles formed in step (a) are constituents of a display library comprising proteins or peptides complexed with eukaryotic ribosomes and the specific mRNAs encoding those proteins or peptides.

13. A method according to claim 12 wherein the mRNA molecules in the display library of step (a) lack stop codons.

14. A method according to claim 12, wherein the individual proteins in the display library of step (a) comprise proteins capable of binding specifically to ligands, thereby allowing the subsequent selection of individual members of the library by binding to an immobilized ligand.

15. A method according to claim 12, wherein the proteins displayed in the display library of step (a) are antibodies or antibody fragments.

16. A method according to claim 15, wherein the antibodies or fragments in the display library of step (a) are encoded by DNA obtained from lymphocytes.

17. A method according to claim 12, wherein the products displayed in the display library of step (a) are receptors.

18. A method according to claim 12, wherein the products displayed in the display library of step (a) are peptides.

19. A method according to claim 18, wherein the peptides in the display library of step (a) are used for identification and mapping of epitopes recognized by specific antibodies or receptors.

20. A method according to claim 12, wherein the products displayed in the display library of step (a) are protein mutants.

21. A method according to claim 20, wherein a display library is formed in step (a), and individual mutants from the display library are selected in step (c).

22. A method according to claim 12, wherein the DNA expression products in the display library of step (a) are generated by means of mutation of cloned DNA encoding antibodies, receptors or fragments thereof.

23. A method according to claim 12, wherein a eukaryotic ribosome display library is used to select ligands for combining sites or receptors.

24. A method according to claim 12, wherein a ribosome display library is used to isolate genes using binding of translated products to an immobilized antibody or ligand.

25. A method capable of (I) displaying and selecting proteins and peptides and (II) recovering genetic material selected from the group consisting of DNA and mRNA that encodes the proteins or peptides, wherein the method comprises:
   (a) conducting coupled transcription of DNA lacking a stop codon and translating mRNA therefrom in a cell free rabbit reticulocyte system in order to from complexed particles comprising at least one individual nascent protein or peptide associated with (i) one or more ribosomes and (ii) the mRNA encoding the protein or peptide;
   (b) contacting the complexed particles with an immobilized ligand, antigne or antibody;
   (c) selecting complexed particles using binding of the ligand, antigen or antibody to the protein or peptide of the complexed particle; and
   (d) conducting reverse transcription and polymerase chain reaction (RT-PCR) on the mRNA bound in the selected complexed particle from step (c) in order produce DNA encoding the protein or peptide.

26. The method according to claim 25, wherein each complexed particle contains only one ribosome.

27. A method capable of (I) display proteins and peptides and (II) recovering genetic material selected from the group consisting of DNA and mRNA that encodes the proteins or peptides, wherein the method comprises:
   (a) translating an mRNA or an mRNA library in a eukaryotic cell free system in order to form complexed particles, wherein a complexed particle comprises at least one individual nascent protein or peptide associated with (i) one or more ribosomes and (ii) the RNA encoding the protein or peptide;
   (b) contacting the particles with a ligand, antigen or antibody;
   (c) selecting complexed particles using binding of the ligand, antigen or antibody with the protein or peptide of the complexed particle; and
   (d) conducting reverse transcription and polymerase chain reaction (RT-PCR) on the mRNA bound in the selected complexed particle in order to produce DNA encoding the protein or peptide.

28. The method according to claim 27, wherein each complexed particle contains only one ribosome.

29. A method capable of (I) displaying proteins and peptides and (II) recovering genetic material selected from the group consisting of DNA and mRNA that encodes the proteins or peptides, wherein the method comprises:
   (a) transcribing a cDNA or a cDNA library and translating mRNA therefrom in a eukaryotic cell free system in order to form complexed particles, wherein a complexed particle comprises at least one individual nascent protein or peptide associated with (i) one or more ribosomes and (ii) the mRNA encoding the protein or peptide;
   (b) contacting the particles with a ligand, antigen or antibody;
   (c) selecting complexed particles using binding of the ligand, antigen or antibody with the protein or peptide of the complexed particle; and
   (d) conducting reverse transcription and polymerase chain reaction (RT-PCR) on the mRNA bound in the selected complexed particle from step (c) in order to produce DNA encoding the protein or peptide.

30. The method according to claim 29, wherein each complexed particle contains only one ribosome.

31. A method of displaying and selecting proteins and peptides and recovering genetic material that encodes the proteins or peptides, wherein the method comprises:
   (a) transcribing and translating DNA in a cell free system in order to form complexed particles, wherein a complexed particle comprises at least one individual nascent protein or peptide associated with (i) a ribosome and (ii) the mRNA encoding the protein or peptide;
   (b) contacting the complexed particles with a ligand, antigen or antibody;
   (c) selecting complexed particles using binding of the ligand, antigen or antibody with the protein or peptide of the complexed particle;
   (d) conducting reverse transcription and polymerase chain reaction (RT-PCR) on the mRNA bound in the selected complexed particle from step (c) in order produce DNA encoding the protein or peptide; and
   (e) recovering the DNA encoding the protein or peptide.

32. A method according to claim 30, wherein the ligand, antigen, or antibody of step (b) is immobilized on insoluble supports.

33. A method for making mammalian antibodies, wherein the method comprises:
   (a) contacting an animal with an antigen,
   (b) making a DNA library comprising combinations of the $V_H$ and $V_L$ regions of the immunoglobulins of said animal, wherein the regions are linked as single chain Fv or $V_H$/K fragments,
   (c) creating a eukaryotic ribosome display library by in vitro transcription of said DNA library and in vitro translation of mRNA therefrom, such that complexed particles are formed, wherein a complexed particle comprises at least one individual nascent antibody, fragment associated with (i) one or more ribosomes and (ii) the mRNA encoding the antibody fragments,
   (d) selecting complexed particles carrying specific antibody fragments through binding to an antigen or other agent,
   (e) conducting reverse transcription and polymerase chain reaction (RT-PCR) on the mRNA bound in the selected complexed particle from step (d) in order to produce DNA encoding the protein or peptide, and
   f) recovering and expressing the DNA from step (e).

34. A method for making human antibodies, wherein the method comprises (a) contacting with an antigen a transgenic mouse carrying human loci encoding heavy and/or light chains of immunoglobulins as transgenes,
   (b) making a DNA library comprising combinations of the $V_H$ and $V_L$ regions of the human immunoglobulins from the mouse, wherein the regions are linked as single chain Fv or $V_H$/K fragments, (c) creating a eukaryotic ribosome display library by in vitro transcription of said DNA library and in vitro translation of mRNA therefrom, such that complexed particles are formed, wherein a complexed particle comprises at least one individual nascent antibody fragment associated with (i) one or more ribosome and (ii) the mRNA encoding the antibody fragment, (d) selecting such complexed particles carrying specific antibody fragments through binding to an antigen or other agent, (e) conducting reverse transcription and polymerase chain reaction (RT-PCR) on the mRNA bound in the selected complexed particle from step (d) in order to produce DNA encoding the protein or peptide, and f) recovering and expressing the DNA from step (e).

* * * * *